United States Patent
Shalev

(10) Patent No.: US 9,254,209 B2
(45) Date of Patent: Feb. 9, 2016

(54) STENT FIXATION WITH REDUCED PLASTIC DEFORMATION

(75) Inventor: Alon Shalev, Ra'anana (IL)

(73) Assignee: ENDOSPAN LTD., Herzilyia Pituach (IL)

( * ) Notice: Subject to any disclaimer, the term of this patent is extended or adjusted under 35 U.S.C. 154(b) by 0 days.

(21) Appl. No.: 14/130,213

(22) PCT Filed: Jul. 2, 2012

(86) PCT No.: PCT/IL2012/000269
§ 371 (c)(1),
(2), (4) Date: Mar. 4, 2014

(87) PCT Pub. No.: WO2013/005207
PCT Pub. Date: Jan. 10, 2013

(65) Prior Publication Data
US 2014/0172072 A1    Jun. 19, 2014

Related U.S. Application Data

(60) Provisional application No. 61/505,132, filed on Jul. 7, 2011.

(51) Int. Cl.
*A61F 2/954* (2013.01)
*A61F 2/945* (2013.01)
(Continued)

(52) U.S. Cl.
CPC ................. *A61F 2/945* (2013.01); *A61F 2/064* (2013.01); *A61F 2/852* (2013.01);
(Continued)

(58) Field of Classification Search
CPC ........................................ A61F 2/954
See application file for complete search history.

(56) References Cited

U.S. PATENT DOCUMENTS

| | | | |
|---|---|---|---|
| 4,355,426 A | 10/1982 | MacGregor | |
| 4,505,767 A | 3/1985 | Quin | |

(Continued)

FOREIGN PATENT DOCUMENTS

| | | |
|---|---|---|
| CA | 2 497 704 | 3/2004 |
| CN | 2453960 | 10/2001 |

(Continued)

OTHER PUBLICATIONS

An English translation of an Office Action dated Oct. 8, 2014, which issued during the prosecution of Chinese Patent Application No. 201080036970.7.

(Continued)

*Primary Examiner* — Yashita Sharma
*Assistant Examiner* — Wade P Schutte
(74) *Attorney, Agent, or Firm* — Sughrue Mion, PLLC

(57) ABSTRACT

An endovascular stent system (10) includes first and second generally tubular stents members (20, 22), which are shaped so as to define first and second interface sections (40, 42), respectively, which are securely coupleable to each other. The first interface section (40) is shaped so as to define an opening (44). The second interface section (42) is shaped so as to define a neck portion (50). When the first and second stent members (20, 22) are coupled together, the neck portion (50) is at least in part defined by: (a) first ones (72) of structural elements (70), positioned at respective first circumferential locations, which are configured to apply, to the opening (44), distally- and radially-outwardly-directed forces, without applying any proximally-directed forces, and (b) separate from the first structural elements (72), second ones (74) of the structural elements (70), positioned at respective second circumferential locations different from the first circumferential locations, which are configured to apply, to the opening (44), a proximally- and radially-outwardly-directed forces, without applying any distally-directed forces.

27 Claims, 8 Drawing Sheets

(51) Int. Cl.
  *A61F 2/06* (2013.01)
  *A61F 2/852* (2013.01)
  *A61B 17/00* (2006.01)
  *A61B 17/11* (2006.01)
  *A61F 2/07* (2013.01)
  *A61F 2/82* (2013.01)

(52) U.S. Cl.
  CPC ............... *A61B 2017/00867* (2013.01); *A61B 2017/1107* (2013.01); *A61B 2017/1135* (2013.01); *A61F 2002/061* (2013.01); *A61F 2002/072* (2013.01); *A61F 2002/828* (2013.01); *A61F 2250/0039* (2013.01); *A61F 2250/0063* (2013.01)

(56) References Cited

U.S. PATENT DOCUMENTS

| | | |
|---|---|---|
| 4,562,596 A | 1/1986 | Kornberg |
| 4,577,631 A | 3/1986 | Kreamer |
| 4,617,932 A | 10/1986 | Kornberg |
| 4,665,906 A | 5/1987 | Jervis |
| 4,739,762 A | 4/1988 | Palmaz |
| 4,787,899 A | 11/1988 | Lazarus |
| 4,878,906 A | 11/1989 | Lindemann et al. |
| 4,886,062 A | 12/1989 | Wiktor |
| 4,938,740 A | 7/1990 | Melbin |
| 4,969,458 A | 11/1990 | Wiktor |
| 5,042,707 A | 8/1991 | Taheri |
| 5,064,435 A | 11/1991 | Porter |
| 5,104,404 A | 4/1992 | Wolff |
| 5,122,136 A | 6/1992 | Guglielmi et al. |
| 5,133,732 A | 7/1992 | Wiktor |
| 5,234,448 A | 8/1993 | Wholey |
| 5,425,765 A | 6/1995 | Tiefenbrun et al. |
| 5,456,694 A | 10/1995 | Marin |
| 5,486,183 A | 1/1996 | Middleman et al. |
| 5,507,769 A | 4/1996 | Marin et al. |
| 5,509,923 A | 4/1996 | Middleman et al. |
| 5,522,880 A | 6/1996 | Barone et al. |
| 5,527,322 A | 6/1996 | Klein et al. |
| 5,549,662 A | 8/1996 | Fordenbacher |
| 5,554,181 A | 9/1996 | Das |
| 5,556,413 A | 9/1996 | Lam |
| 5,562,724 A | 10/1996 | Vorwerk et al. |
| 5,613,974 A | 3/1997 | Andreas et al. |
| 5,632,746 A | 5/1997 | Middleman et al. |
| 5,632,763 A | 5/1997 | Glastra |
| 5,632,772 A | 5/1997 | Alcime et al. |
| 5,639,278 A | 6/1997 | Dereume et al. |
| 5,643,340 A | 7/1997 | Nunokawa |
| 5,653,743 A | 8/1997 | Martin |
| 5,676,696 A | 10/1997 | Marcade |
| 5,676,697 A | 10/1997 | McDonald |
| 5,728,134 A | 3/1998 | Barak |
| 5,749,879 A | 5/1998 | Middleman et al. |
| 5,755,770 A | 5/1998 | Ravenscroft |
| 5,755,771 A | 5/1998 | Penn et al. |
| 5,755,774 A | 5/1998 | Pinchuk |
| 5,755,777 A | 5/1998 | Chuter |
| 5,755,781 A | 5/1998 | Jayaraman |
| 5,769,882 A | 6/1998 | Fogarty et al. |
| 5,782,903 A | 7/1998 | Wiktor |
| 5,782,906 A | 7/1998 | Marshall et al. |
| 5,824,040 A | 10/1998 | Cox et al. |
| 5,827,321 A | 10/1998 | Roubin |
| 5,843,170 A | 12/1998 | Ahn |
| 5,855,600 A | 1/1999 | Alt |
| 5,860,991 A | 1/1999 | Klein et al. |
| 5,876,432 A | 3/1999 | Lau et al. |
| 5,906,641 A | 5/1999 | Thompson et al. |
| 5,921,994 A | 7/1999 | Andreas et al. |
| 5,948,018 A | 9/1999 | Dereume et al. |
| 5,976,178 A | 11/1999 | Goldsteen et al. |
| 5,980,552 A | 11/1999 | Pinchasik |
| 5,984,955 A | 11/1999 | Wisselink |
| 6,015,431 A | 1/2000 | Thornton et al. |
| 6,016,810 A | 1/2000 | Ravenscroft |
| 6,030,414 A | 2/2000 | Taheri |
| 6,033,435 A | 3/2000 | Penn et al. |
| 6,036,725 A | 3/2000 | Avellanet |
| 6,059,824 A | 5/2000 | Taheri |
| 6,077,298 A | 6/2000 | Tu |
| 6,099,497 A | 8/2000 | Adams et al. |
| 6,099,548 A | 8/2000 | Taheri |
| 6,117,145 A | 9/2000 | Wood et al. |
| 6,168,615 B1 | 1/2001 | Ken |
| 6,200,339 B1 | 3/2001 | Leschinsky et al. |
| 6,206,893 B1 | 3/2001 | Klein et al. |
| 6,270,524 B1 | 8/2001 | Kim |
| 6,283,991 B1 | 9/2001 | Cox et al. |
| 6,290,720 B1 | 9/2001 | Khosravi et al. |
| 6,296,661 B1 | 10/2001 | Davila |
| 6,319,287 B1 | 11/2001 | Frimberger |
| 6,325,823 B1 | 12/2001 | Horzewski et al. |
| 6,344,056 B1 | 2/2002 | Dehdashtian |
| 6,406,420 B1 | 6/2002 | McCarthy |
| 6,428,565 B1 | 8/2002 | Wisselink |
| 6,451,048 B1 | 9/2002 | Berg et al. |
| 6,506,211 B1 | 1/2003 | Skubitz et al. |
| 6,565,597 B1 | 5/2003 | Fearnot et al. |
| 6,613,075 B1 | 9/2003 | Healy et al. |
| 6,613,078 B1 | 9/2003 | Barone |
| 6,635,083 B1 | 10/2003 | Cheng et al. |
| 6,648,901 B2 | 11/2003 | Fleischman et al. |
| 6,652,567 B1 | 11/2003 | Deaton |
| 6,656,214 B1 | 12/2003 | Fogarty et al. |
| 6,692,520 B1 | 2/2004 | Gambale et al. |
| 6,695,833 B1 | 2/2004 | Frantzen |
| 6,730,117 B1 | 5/2004 | Tseng et al. |
| 6,733,523 B2 | 5/2004 | Shaolian |
| 6,743,195 B2 | 6/2004 | Zucker |
| 6,748,953 B2 | 6/2004 | Sherry et al. |
| 6,752,826 B2 | 6/2004 | Holloway |
| 6,776,794 B1 | 8/2004 | Hong et al. |
| 6,814,749 B2 | 11/2004 | Cox et al. |
| 6,814,752 B1 | 11/2004 | Chuter |
| 6,824,560 B2 | 11/2004 | Pelton |
| 6,846,321 B2 | 1/2005 | Zucker |
| 6,907,285 B2 | 6/2005 | Denker et al. |
| 6,908,477 B2 | 6/2005 | McGuckin, Jr. et al. |
| 6,929,660 B1 | 8/2005 | Ainsworth et al. |
| 6,942,691 B1 | 9/2005 | Chuter |
| 6,953,469 B2 | 10/2005 | Ryan |
| 6,964,679 B1 | 11/2005 | Marcade et al. |
| 6,986,774 B2 | 1/2006 | Middleman et al. |
| 7,008,441 B2 | 3/2006 | Zucker |
| 7,022,131 B1 | 4/2006 | Derowe et al. |
| 7,044,962 B2 | 5/2006 | Elliott |
| 7,105,020 B2 | 9/2006 | Greenberg et al. |
| 7,112,217 B1 | 9/2006 | Kugler et al. |
| 7,115,127 B2 | 10/2006 | Lindenbaum et al. |
| 7,144,421 B2 | 12/2006 | Carpenter et al. |
| 7,160,318 B2 | 1/2007 | Greenberg |
| 7,201,772 B2 | 4/2007 | Schwammenthal et al. |
| 7,223,266 B2 | 5/2007 | Lindenbaum et al. |
| 7,261,733 B1 | 8/2007 | Brown |
| 7,270,675 B2 | 9/2007 | Chun |
| 7,279,003 B2 | 10/2007 | Berra et al. |
| 7,294,147 B2 | 11/2007 | Hartley |
| 7,306,623 B2 | 12/2007 | Watson |
| 7,341,598 B2 | 3/2008 | Davidson et al. |
| 7,399,313 B2 | 7/2008 | Brown |
| 7,407,509 B2 | 8/2008 | Greenberg et al. |
| 7,425,219 B2 | 9/2008 | Quadri |
| 7,429,269 B2 | 9/2008 | Schwammenthal et al. |
| 7,438,721 B2 | 10/2008 | Doig |
| 7,442,204 B2 | 10/2008 | Schwammenthal et al. |
| 7,473,272 B2 | 1/2009 | Pryor |
| 7,537,609 B2 | 5/2009 | Davidson et al. |
| 7,540,881 B2 | 6/2009 | Meyer et al. |
| 7,544,160 B2 | 6/2009 | Gross |
| 7,616,997 B2 | 11/2009 | Kieval |
| 7,637,939 B2 | 12/2009 | Tischler |

(56) References Cited

U.S. PATENT DOCUMENTS

| | | |
|---|---|---|
| 7,645,298 B2 | 1/2010 | Hartley et al. |
| 7,662,161 B2 | 2/2010 | Briganti et al. |
| 7,662,168 B2 | 2/2010 | McGuckin, Jr. et al. |
| 7,678,141 B2 | 3/2010 | Greenan et al. |
| 7,708,704 B2 | 5/2010 | Mitelberg |
| 7,722,626 B2 | 5/2010 | Middleman et al. |
| 7,731,732 B2 | 6/2010 | Ken |
| 7,803,178 B2 | 9/2010 | Whirley |
| 7,815,673 B2 | 10/2010 | Bloom et al. |
| 7,959,662 B2 | 6/2011 | Erbel et al. |
| 8,021,418 B2 | 9/2011 | Gerberding |
| 8,052,741 B2 | 11/2011 | Bruszewski et al. |
| 8,066,755 B2 | 11/2011 | Zacharias |
| 8,080,026 B2 | 12/2011 | Konstantino |
| 8,080,053 B2 | 12/2011 | Satasiya |
| 8,157,810 B2 | 4/2012 | Case |
| 8,172,892 B2 | 5/2012 | Chuter |
| 8,236,040 B2 | 8/2012 | Mayberry |
| 8,251,963 B2 | 8/2012 | Chin |
| 8,337,546 B2 | 12/2012 | Bruszewski |
| 8,353,898 B2 | 1/2013 | Lutze |
| 2001/0000188 A1 | 4/2001 | Lenker |
| 2001/0004705 A1 | 6/2001 | Killion |
| 2001/0010006 A1 | 7/2001 | Bachinski et al. |
| 2001/0014823 A1 | 8/2001 | Ressemann et al. |
| 2001/0037142 A1 | 11/2001 | Stelter et al. |
| 2001/0044651 A1 | 11/2001 | Steinke |
| 2001/0044652 A1 | 11/2001 | Moore |
| 2001/0047198 A1 | 11/2001 | Drasler |
| 2001/0049550 A1 | 12/2001 | Martin |
| 2001/0053930 A1 | 12/2001 | Kugler et al. |
| 2002/0040236 A1 | 4/2002 | Lau |
| 2002/0052643 A1 | 5/2002 | Wholey |
| 2002/0072790 A1 | 6/2002 | McGuckin |
| 2002/0099441 A1 | 7/2002 | Dehdashtian |
| 2002/0107564 A1 | 8/2002 | Cox |
| 2002/0111667 A1 | 8/2002 | Girton |
| 2002/0123791 A1 | 9/2002 | Harrison |
| 2002/0156495 A1 | 10/2002 | Brenneman et al. |
| 2002/0156517 A1 | 10/2002 | Perouse |
| 2002/0173809 A1 | 11/2002 | Fleischman |
| 2002/0193864 A1 | 12/2002 | Khosravi |
| 2002/0198585 A1 | 12/2002 | Wisselink |
| 2003/0033005 A1 | 2/2003 | Houser et al. |
| 2003/0040791 A1 | 2/2003 | Oktay |
| 2003/0057156 A1 | 3/2003 | Peterson et al. |
| 2003/0093145 A1 | 5/2003 | Lawrence-Brown et al. |
| 2003/0125796 A1 | 7/2003 | Dong |
| 2003/0130720 A1 | 7/2003 | DePalma et al. |
| 2003/0153968 A1 | 8/2003 | Geis et al. |
| 2003/0163187 A1 | 8/2003 | Weber |
| 2003/0191523 A1 | 10/2003 | Hojeibane |
| 2003/0199967 A1 | 10/2003 | Hartley et al. |
| 2003/0212449 A1 | 11/2003 | Cox |
| 2003/0236567 A1 | 12/2003 | Elliot |
| 2004/0015227 A1 | 1/2004 | Vardi et al. |
| 2004/0015229 A1 | 1/2004 | Fulkerson |
| 2004/0098091 A1 | 5/2004 | Erbel |
| 2004/0106972 A1 | 6/2004 | Deaton |
| 2004/0106978 A1 | 6/2004 | Greenberg et al. |
| 2004/0117003 A1 | 6/2004 | Ouriel |
| 2004/0133266 A1 | 7/2004 | Clerc et al. |
| 2004/0138735 A1 | 7/2004 | Shaolian |
| 2004/0162606 A1 | 8/2004 | Thompson |
| 2004/0171978 A1 | 9/2004 | Shalaby |
| 2004/0176832 A1 | 9/2004 | Hartley et al. |
| 2004/0181149 A1 | 9/2004 | Langlotz et al. |
| 2004/0215319 A1 | 10/2004 | Berra |
| 2004/0215327 A1 | 10/2004 | Doig et al. |
| 2004/0260383 A1 | 12/2004 | Stelter |
| 2005/0033406 A1 | 2/2005 | Barnhart et al. |
| 2005/0049678 A1 | 3/2005 | Cocks et al. |
| 2005/0065545 A1 | 3/2005 | Wallace |
| 2005/0070995 A1 | 3/2005 | Zilla et al. |
| 2005/0085900 A1 | 4/2005 | Case |
| 2005/0102018 A1 | 5/2005 | Carpenter et al. |
| 2005/0102021 A1 | 5/2005 | Osborne |
| 2005/0131512 A1 | 6/2005 | Vonderwalde |
| 2005/0131517 A1 | 6/2005 | Hartley et al. |
| 2005/0143802 A1 | 6/2005 | Soykan |
| 2005/0149166 A1 | 7/2005 | Schaeffer et al. |
| 2005/0154448 A1 | 7/2005 | Cully |
| 2005/0159803 A1 | 7/2005 | Lad |
| 2005/0165480 A1 | 7/2005 | Jordan |
| 2005/0171598 A1 | 8/2005 | Schaeffer et al. |
| 2005/0171599 A1 | 8/2005 | White |
| 2005/0177132 A1 | 8/2005 | Lentz |
| 2005/0177222 A1 | 8/2005 | Mead |
| 2005/0203606 A1 | 9/2005 | VanCamp |
| 2005/0216018 A1 | 9/2005 | Sennett |
| 2005/0222649 A1 | 10/2005 | Capuano |
| 2005/0222667 A1 | 10/2005 | Hunt |
| 2005/0222668 A1 | 10/2005 | Schaeffer et al. |
| 2005/0222669 A1 | 10/2005 | Purdy |
| 2005/0234542 A1 | 10/2005 | Melsheimer |
| 2005/0266042 A1 | 12/2005 | Tseng |
| 2005/0273155 A1 | 12/2005 | Bahler |
| 2006/0015170 A1 | 1/2006 | Jones et al. |
| 2006/0030921 A1 | 2/2006 | Chu |
| 2006/0052799 A1 | 3/2006 | Middleman et al. |
| 2006/0069426 A1 | 3/2006 | Weinberger |
| 2006/0095104 A1 | 5/2006 | Magers |
| 2006/0095114 A1 | 5/2006 | Hartley et al. |
| 2006/0100684 A1 | 5/2006 | Elliott |
| 2006/0116748 A1 | 6/2006 | Kaplan |
| 2006/0149360 A1 | 7/2006 | Schwammenthal et al. |
| 2006/0155358 A1 | 7/2006 | LaDuca et al. |
| 2006/0155359 A1 | 7/2006 | Watson |
| 2006/0155366 A1 | 7/2006 | LaDuca et al. |
| 2006/0167476 A1 | 7/2006 | Burdulis, Jr. et al. |
| 2006/0173530 A1 | 8/2006 | Das |
| 2006/0190070 A1 | 8/2006 | Dieck |
| 2006/0193892 A1 | 8/2006 | Furst et al. |
| 2006/0229709 A1 | 10/2006 | Morris et al. |
| 2006/0241740 A1 | 10/2006 | Vardi et al. |
| 2006/0271166 A1 | 11/2006 | Thill |
| 2006/0281966 A1 | 12/2006 | Peacock, III |
| 2007/0016281 A1 | 1/2007 | Melsheimer |
| 2007/0021822 A1 | 1/2007 | Boatman |
| 2007/0043425 A1 | 2/2007 | Hartley et al. |
| 2007/0050011 A1 | 3/2007 | Klein |
| 2007/0055326 A1 | 3/2007 | Farley |
| 2007/0055350 A1 | 3/2007 | Erickson et al. |
| 2007/0055358 A1 | 3/2007 | Krolik et al. |
| 2007/0055360 A1 | 3/2007 | Hanson |
| 2007/0060989 A1 | 3/2007 | Deem et al. |
| 2007/0061002 A1 | 3/2007 | Paul |
| 2007/0067014 A1 | 3/2007 | Ke et al. |
| 2007/0073373 A1 | 3/2007 | Bonsignore |
| 2007/0088425 A1 | 4/2007 | Schaeffer |
| 2007/0106368 A1 | 5/2007 | Vonderwalde |
| 2007/0112344 A1 | 5/2007 | Keilman |
| 2007/0135677 A1 | 6/2007 | Miller et al. |
| 2007/0142896 A1 | 6/2007 | Anderson et al. |
| 2007/0150051 A1 | 6/2007 | Arnault de la et al. |
| 2007/0156167 A1 | 7/2007 | Connors et al. |
| 2007/0167898 A1 | 7/2007 | Peters et al. |
| 2007/0167955 A1 | 7/2007 | Menardiere |
| 2007/0168018 A1 | 7/2007 | Amplatz et al. |
| 2007/0179598 A1 | 8/2007 | Duerig |
| 2007/0185565 A1 | 8/2007 | Schwammenthal et al. |
| 2007/0207186 A1 | 9/2007 | Scanlon |
| 2007/0208410 A1 | 9/2007 | Berra et al. |
| 2007/0213805 A1 | 9/2007 | Schaeffer et al. |
| 2007/0213807 A1 | 9/2007 | Roubin |
| 2007/0219610 A1 | 9/2007 | Israel |
| 2007/0225797 A1 | 9/2007 | Krivoruhko |
| 2007/0233229 A1 | 10/2007 | Berra et al. |
| 2007/0237973 A1 | 10/2007 | Purdy |
| 2007/0239256 A1 | 10/2007 | Weber |
| 2007/0244542 A1 | 10/2007 | Greenan et al. |
| 2007/0244543 A1 | 10/2007 | Mitchell |
| 2007/0244547 A1 | 10/2007 | Greenan |
| 2007/0250154 A1 | 10/2007 | Greenberg |

(56) References Cited

U.S. PATENT DOCUMENTS

| | | |
|---|---|---|
| 2007/0255388 A1 | 11/2007 | Rudakov et al. |
| 2008/0002871 A1 | 1/2008 | Gunzert-Marx et al. |
| 2008/0015673 A1 | 1/2008 | Chuter |
| 2008/0033527 A1 | 2/2008 | Nunez |
| 2008/0058918 A1 | 3/2008 | Watson |
| 2008/0064957 A1 | 3/2008 | Spence |
| 2008/0086193 A1 | 4/2008 | Thramann |
| 2008/0109066 A1 | 5/2008 | Quinn |
| 2008/0114444 A1 | 5/2008 | Yu |
| 2008/0114445 A1 | 5/2008 | Melsheimer et al. |
| 2008/0114446 A1 | 5/2008 | Hartley et al. |
| 2008/0140178 A1 | 6/2008 | Rasmussen et al. |
| 2008/0147173 A1 | 6/2008 | McIff et al. |
| 2008/0167704 A1 | 7/2008 | Wright et al. |
| 2008/0176271 A1 | 7/2008 | Silver |
| 2008/0195191 A1 | 8/2008 | Luo |
| 2008/0262595 A1 | 10/2008 | Chu et al. |
| 2008/0262598 A1 | 10/2008 | Elmaleh |
| 2008/0269789 A1 | 10/2008 | Eli |
| 2008/0275540 A1 | 11/2008 | Wen |
| 2008/0275542 A1 | 11/2008 | LaDuca et al. |
| 2008/0288044 A1 | 11/2008 | Osborne |
| 2008/0294234 A1 | 11/2008 | Hartley et al. |
| 2008/0300665 A1 | 12/2008 | Lootz |
| 2008/0312732 A1 | 12/2008 | Hartley et al. |
| 2008/0319528 A1 | 12/2008 | Yribarren et al. |
| 2009/0012597 A1 | 1/2009 | Doig et al. |
| 2009/0012602 A1 | 1/2009 | Quadri |
| 2009/0030497 A1 | 1/2009 | Metcalf |
| 2009/0030502 A1 | 1/2009 | Sun et al. |
| 2009/0048663 A1 | 2/2009 | Greenberg |
| 2009/0054967 A1 | 2/2009 | Das |
| 2009/0069881 A1 | 3/2009 | Chalekian |
| 2009/0069882 A1 | 3/2009 | Venturelli |
| 2009/0082841 A1 | 3/2009 | Zacharias |
| 2009/0099648 A1 | 4/2009 | Yu |
| 2009/0099649 A1 | 4/2009 | Chobotov et al. |
| 2009/0099650 A1 | 4/2009 | Bolduc |
| 2009/0105809 A1 | 4/2009 | Lee et al. |
| 2009/0112233 A1 | 4/2009 | Xiao |
| 2009/0125096 A1 | 5/2009 | Chu et al. |
| 2009/0138067 A1 | 5/2009 | Pinchuk et al. |
| 2009/0149877 A1 | 6/2009 | Hanson et al. |
| 2009/0157014 A1 | 6/2009 | Osborne et al. |
| 2009/0227997 A1 | 9/2009 | Wang |
| 2009/0240316 A1 | 9/2009 | Bruszewski |
| 2009/0248134 A1 | 10/2009 | Dierking et al. |
| 2009/0254170 A1 | 10/2009 | Hartley et al. |
| 2009/0259290 A1 | 10/2009 | Bruszewski et al. |
| 2009/0287145 A1 | 11/2009 | Cragg et al. |
| 2009/0319022 A1 | 12/2009 | Hartley et al. |
| 2010/0004728 A1 | 1/2010 | Rao |
| 2010/0029608 A1 | 2/2010 | Finley |
| 2010/0057186 A1 | 3/2010 | West et al. |
| 2010/0063575 A1 | 3/2010 | Shalev |
| 2010/0070019 A1 | 3/2010 | Shalev |
| 2010/0161025 A1 | 6/2010 | Kuppurathanam et al. |
| 2010/0161026 A1 | 6/2010 | Brocker et al. |
| 2010/0161028 A1 | 6/2010 | Chuter et al. |
| 2010/0249899 A1 | 9/2010 | Chuter et al. |
| 2010/0256725 A1 | 10/2010 | Rasmussen |
| 2010/0268327 A1 | 10/2010 | Bruszewski et al. |
| 2010/0274187 A1 | 10/2010 | Argentine |
| 2010/0274345 A1 | 10/2010 | Rust |
| 2010/0292774 A1 | 11/2010 | Shalev |
| 2010/0312326 A1 | 12/2010 | Chuter et al. |
| 2011/0022149 A1 | 1/2011 | Cox |
| 2011/0093002 A1 | 4/2011 | Rucker et al. |
| 2011/0125251 A1 | 5/2011 | Cottone |
| 2011/0152998 A1 | 6/2011 | Berez et al. |
| 2011/0208289 A1 | 8/2011 | Shalev |
| 2011/0208296 A1 | 8/2011 | Duffy et al. |
| 2011/0208297 A1 | 8/2011 | Tuval et al. |
| 2011/0208298 A1 | 8/2011 | Tuval et al. |
| 2011/0218607 A1 | 9/2011 | Arbefeuille et al. |
| 2011/0257720 A1 | 10/2011 | Peterson |
| 2011/0257725 A1 | 10/2011 | Argentine |
| 2011/0262684 A1 | 10/2011 | Wintsch |
| 2011/0264184 A1 | 10/2011 | Heltai |
| 2011/0270385 A1 | 11/2011 | Muzslay |
| 2011/0288622 A1 | 11/2011 | Chan |
| 2011/0301702 A1 | 12/2011 | Rust |
| 2011/0319983 A1 | 12/2011 | Zhu |
| 2012/0143317 A1 | 6/2012 | Cam |
| 2012/0150274 A1 | 6/2012 | Shalev |
| 2012/0158038 A1 | 6/2012 | Leschinsky |
| 2012/0172929 A1 | 7/2012 | Shalev |
| 2012/0179236 A1 | 7/2012 | Shalev |
| 2012/0185031 A1 | 7/2012 | Ryan |
| 2012/0271401 A1 | 10/2012 | Bruszewski |
| 2012/0310324 A1 | 12/2012 | Shalev |
| 2012/0316634 A1 | 12/2012 | Shalev |
| 2012/0323305 A1 | 12/2012 | Shalev |
| 2012/0330399 A1 | 12/2012 | Shalev |
| 2013/0013050 A1 | 1/2013 | Shalev |
| 2013/0013051 A1 | 1/2013 | Benary |
| 2013/0035751 A1 | 2/2013 | Shalev |
| 2013/0090722 A1 | 4/2013 | Shalev |
| 2013/0131783 A1 | 5/2013 | Shalev |
| 2013/0158646 A1 | 6/2013 | Roeder |
| 2013/0204343 A1 | 8/2013 | Shalev |
| 2013/0261994 A1 | 10/2013 | Shalev |
| 2013/0274866 A1 | 10/2013 | Cox |
| 2013/0289587 A1 | 10/2013 | Shalev |
| 2014/0350658 A1 | 11/2014 | Benary et al. |
| 2014/0364930 A1 | 12/2014 | Strauss |
| 2015/0073534 A1 | 3/2015 | Roeder et al. |

FOREIGN PATENT DOCUMENTS

| | | |
|---|---|---|
| CN | 2817770 Y | 9/2006 |
| EP | 1 177 780 | 2/2002 |
| EP | 1 325 716 | 7/2003 |
| JP | 2002-253682 | 9/2002 |
| WO | 98/06355 A1 | 2/1998 |
| WO | 99/34748 A1 | 7/1999 |
| WO | 00/28923 A1 | 5/2000 |
| WO | 02/083038 | 10/2002 |
| WO | 03/099108 | 12/2003 |
| WO | 2004/017868 | 3/2004 |
| WO | 2005/002466 | 1/2005 |
| WO | 2005/037138 | 4/2005 |
| WO | 2005/041781 | 5/2005 |
| WO | 2005/041783 | 5/2005 |
| WO | 2006/007389 | 1/2006 |
| WO | 2006/028925 | 3/2006 |
| WO | 2006/070372 | 7/2006 |
| WO | 2007/084547 | 7/2007 |
| WO | 2007/144782 | 12/2007 |
| WO | 2008/008291 | 1/2008 |
| WO | 2008/035337 | 3/2008 |
| WO | 2008/042266 | 4/2008 |
| WO | 2008/047092 | 4/2008 |
| WO | 2008/047354 | 4/2008 |
| WO | 2008/053469 | 5/2008 |
| WO | 2008/066923 | 6/2008 |
| WO | 2008/107885 | 9/2008 |
| WO | 2008/140796 | 11/2008 |
| WO | 2009/078010 | 6/2009 |
| WO | 2009/116041 | 9/2009 |
| WO | 2009/116042 | 9/2009 |
| WO | 2009/118733 | 10/2009 |
| WO | 2010/024869 | 3/2010 |
| WO | 2010/024879 | 3/2010 |
| WO | 2010/031060 | 3/2010 |
| WO | 2010/045238 | 4/2010 |
| WO | 2010/062355 | 6/2010 |
| WO | 2010/088776 | 8/2010 |
| WO | 2010128162 | 11/2010 |
| WO | 2010/150208 | 12/2010 |
| WO | 2011/004374 | 1/2011 |
| WO | 2011/007354 | 1/2011 |
| WO | 2011/055364 | 5/2011 |
| WO | 2011/064782 | 6/2011 |

(56) References Cited

FOREIGN PATENT DOCUMENTS

| | | |
|---|---|---|
| WO | 2011/067764 | 6/2011 |
| WO | 2011/070576 | 6/2011 |
| WO | 2011/080738 | 7/2011 |
| WO | 2011/095979 | 8/2011 |
| WO | 2011/106532 | 9/2011 |
| WO | 2011/106533 | 9/2011 |
| WO | 2011/106544 | 9/2011 |
| WO | 2012/117395 | 7/2012 |
| WO | 2012/104842 | 8/2012 |
| WO | 2012/111006 | 8/2012 |
| WO | 2012/176187 | 12/2012 |
| WO | 2013/084235 | 6/2013 |
| WO | 2013/171730 | 11/2013 |

OTHER PUBLICATIONS

An International Search Report dated Sep. 29, 2008, which issued during the prosecution of Applicant's PCT/IL08/000287.
A Written Opinion dated Sep. 29, 2008, which issued during the prosecution of Applicant's PCT/IL08/000287.
An International Search Report dated Feb. 4, 2011, which issued during the prosecution of Applicant's PCT/IB2010/052861.
U.S. Appl. No. 61/505,132, filed Jul. 7, 2011.
A Written Opinion dated Feb. 4, 2011, which issued during the prosecution of Applicant's PCT/IB2010/052861.
An International Search Report dated Dec. 3, 2010, which issued during the prosecution of Applicant's PCT/IL2010/000564.
A Written Opinion dated Dec. 3, 2010, which issued during the prosecution of Applicant's PCT/IL2010/000564.
An International Search Report dated Nov. 5, 2010, which issued during the prosecution of Applicant's PCT/IL2010/000549.
A Written Opinion dated Nov. 5, 2010, which issued during the prosecution of Applicant's PCT/IL2010/000549.
An International Search Report and Written Opinion both dated Aug. 4, 2011, which issued during the prosecution of Applicant's PCT/IL2010/000999.
An International Search Report and Written Opinion both dated Mar. 10, 2011, which issued during the prosecution of Applicant's PCT/IL2010/000917.
An International Search Report and Written Opinion both dated Mar. 30, 2011, which issued during the prosecution of Applicant's PCT/IL2010/001018.
An International Search Report and Written Opinion both dated Apr. 18, 2011, which issued during the prosecution of Applicant's PCT/IL2010/001037.
An International Search Report and Written Opinion both dated May 23, 2011, which issued during the prosecution of Applicant's PCT/IL2010/001087.
An International Search Report and Written Opinion both dated Jun. 28, 2011, which issued during the prosecution of Applicant's PCT/IL2011/000135.
An International Search Report dated Jun. 30, 2009, which issued during the prosecution of Applicant's PCT/IL2008/001621.
A Written Opinion dated Jun. 30, 2009, which issued during the prosecution of Applicant's PCT/IL2008/001621.
An International Search Report dated Mar. 11, 2009, which issued during the prosecution of Applicant's PCT/IL2007/001312.
A Written Opinion dated Mar. 11, 2009, which issued during the prosecution of Applicant's PCT/IL2007/001312.
An Office Action dated Mar. 24, 2011, which issued during the prosecution of U.S. Appl. No. 12/529,936.
An Office Action dated Oct. 28, 2011, which issued during the prosecution of U.S. Appl. No. 12/529,936.
An English translation of an Office Action dated Aug. 25, 2011, which issued during the prosecution of Chinese Patent Application No. 200880014919.9.
An Office Action dated Nov. 12, 2010, which issued during the prosecution of U.S. Appl. No. 12/447,684.
An Office Action dated Apr. 27, 2011, which issued during the prosecution of U.S. Appl. No. 12/447,684.

"E-vita® open plus" product brochure (JOTEC GmbH, Hechingen, Germany), 2010.
Fonseca A et al., "Intravascular ultrasound assessment of the novel AngioSculpt scoring balloon catheter for the treatment of complex coronary lesions," J Invasive Cardiol 20(1):21-7 (Jan. 2008).
Khlif H et al., "Contribution to the Improvement of Textile Vascular Prostheses Crimping," Trends in Applied Sciences Research 6(9):1019-1027 (2011).
An International Search Report together with Written Opinion both dated Aug. 31, 2012, which issued during the prosecution of Applicant's PCT/IL2012/000148.
An International Search Report together with Written Opinion both dated Sep. 6, 2012, which issued during the prosecution of Applicant's PCT/IL2012/000190.
An International Search Report together with Written Opinion both dated Sep. 24, 2012, which issued during the prosecution of Applicant's PCT/IL2012/000060.
An International Search Report together with Written Opinion both dated Jun. 14, 2013, which issued during the prosecution of Applicant's PCT/IL2012/050506.
An Office Action dated Feb. 28, 2014, which issued during the prosecution of U.S. Appl. No. 13/512,778.
An International Search Report together with Written Opinion both dated Oct. 4, 2012, which issued during the prosecution of Applicant's PCT/IL2012/000269.
An International Search Report together with Written Opinion both dated Mar. 15, 2013, which issued during the prosecution of Applicant's PCT/IL2012/050424.
An International Search Report together with Written Opinion both dated Nov. 26, 2013, which issued during the prosecution of Applicant's PCT/IL2013/050656.
Notice of Allowance dated Aug. 2, 2012, which issued during the prosecution of U.S. Appl. No. 12/529,936.
Notice of Allowance dated Aug. 18, 2013, which issued during the prosecution of U.S. Appl. No. 13/523,296.
An Office Action dated May 20, 2013, which issued during the prosecution of U.S. Appl. No. 13/807,880.
An Office Action dated Dec. 2, 2013, which issued during the prosecution of U.S. Appl. No. 13/807,880.
An Advisory Action dated Feb. 13, 2014, which issued during the prosecution of U.S. Appl. No. 13/807,880.
An English translation of an Office Action dated Feb. 16, 2013, which issued during the prosecution of Chinese Patent Application No. 200880126889.0.
An English translation of an Office Action dated Nov. 28, 2013, which issued during the prosecution of Chinese Patent Application No. 200880126889.0.
An English translation of an Office Action dated May 16, 2014, which issued during the prosecution of Chinese Patent Application No. 200880126889.0.
Supplementary European Search Report dated Dec. 13, 2012 which issued during the prosecution of Applicant's European App No. 08 71 9912.
Invitation to Pay Additional Fees dated May 8, 2014, which issued during the prosecution of Applicant's PCT/IL2014/50174.
Invitation to Pay Additional Fees dated May 13, 2014, which issued during the prosecution of Applicant's PCT/IL2014/050019.
An Office Action dated Oct. 11, 2012, which issued during the prosecution of U.S. Appl. No. 13/031,871.
An Office Action dated Feb. 25, 2013, which issued during the prosecution of U.S. Appl. No. 13/031,871.
An Office Action dated Jul. 28, 2014, which issued during the prosecution of U.S. Appl. No. 13/031,871.
International Search Report and Written Opinion dated Mar. 18, 2015 from the International Searching Authority in counterpart application No. PCT/IL2014/050973.
Communication dated Feb. 5, 2015 from the United States Patent and Trademark Office in counterpart U.S. Appl. No. 13/384,075.
Communication dated Mar. 20, 2015 from the European Patent Office in counterpart application No. 08861980.4.

(56) References Cited

OTHER PUBLICATIONS

Communication dated May 15, 2015 from the United States Patent and Trademark Office in counterpart U.S. Appl. No. 13/577,161.
Communication dated Mar. 26, 2015 from the United States Patent and Trademark Office in counterpart U.S. Appl. No. 13/514,240.
Communication dated Feb. 26, 2015 from the European Patent Office in counterpart Application No. 12806964.8.
Communication dated Mar. 19, 2015 from the State Intellectual Property Office of the People's Republic of China in counterpart application No. 201080036970.7.
Communication dated Jul. 30, 2015 from the United States Patent and Trademark Office in counterpart U.S. Appl. No. 14/240,600.
Communication dated May 28, 2015 from the United States Patent and Trademark Office in counterpart U.S. Appl. No. 14/240,600.
Communication dated Aug. 12, 2015 from the United States Patent and Trademark Office in counterpart U.S. Appl. No. 13/513,397.
International Search Report and Written Opinion dated Jul. 30, 2014 from the International Searching Authority in counterpart application No. PCT/IL2014/050174.
Communication dated Jun. 12, 2015 from the European Patent Office in counterpart application No. 12855964.8.
Communication dated Feb. 23, 2015 from the United States Patent and Trademark Office in counterpart U.S. Appl. No. 13/513,397.
Communication dated Apr. 22, 2015 from the European Patent Office in counterpart application No. 12828495.7.
Communication dated Sep. 23, 2015, issued by the U.S. Patent and Trademark Office in corresponding U.S. Appl. No. 13/384,075.
Communication dated Oct. 2, 2015, issued by the U.S. Patent and Trademark Office in corresponding U.S. Appl. No. 13/577,161.
Interview Minutes issued Dec. 1, 2015 in parallel European Appl. No. 12806964.8.

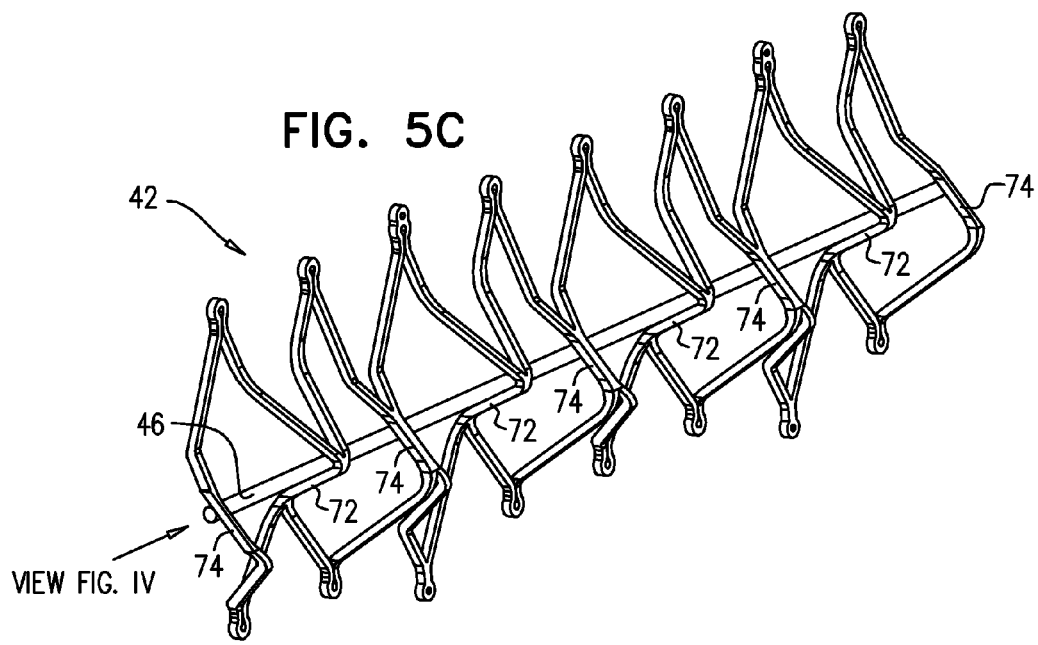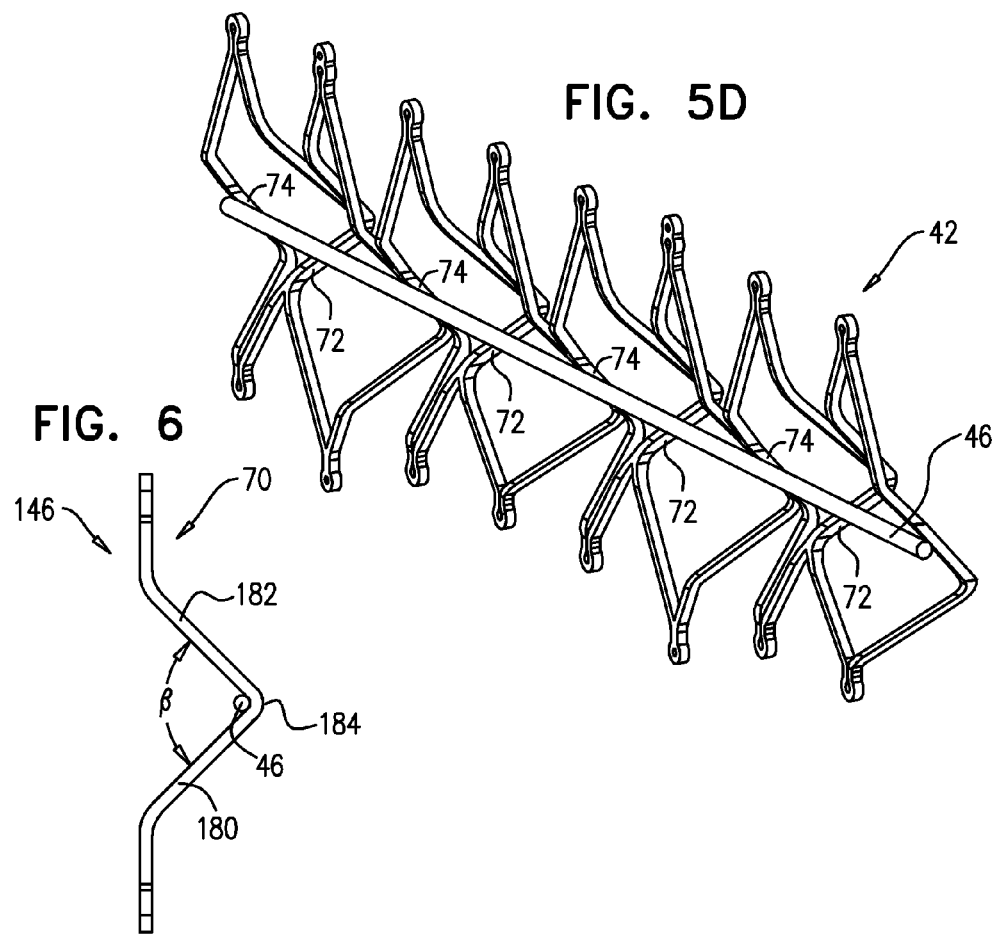

STENT FIXATION WITH REDUCED PLASTIC DEFORMATION

CROSS-REFERENCE TO RELATED APPLICATIONS

The present application is the U.S. national stage of International Application PCT/IL2012/000269, filed Jul. 2, 2012, which claims priority from U.S. Provisional Patent Application 61/505,132, filed Jul. 7, 2011, which is assigned to the assignee of the present application and is incorporated herein by reference.

FIELD OF THE APPLICATION

The present application relates generally to prostheses and surgical methods, and specifically to tubular prostheses, including endovascular grafts and stent-grafts, and surgical techniques for using the prostheses to maintain patency of body passages such as blood vessels, and treating aneurysms.

BACKGROUND OF THE APPLICATION

Endovascular prostheses are sometimes used to treat aortic aneurysms. Such treatment includes implanting a stent or stent-graft within the diseased vessel to bypass the anomaly. An aneurysm is a sac formed by the dilation of the wall of the artery. Aneurysms may be congenital, but are usually caused by disease or, occasionally, by trauma. Aortic aneurysms which commonly form between the renal arteries and the iliac arteries are referred to as abdominal aortic aneurysms ("AAAs"). Other aneurysms occur in the aorta, such as thoracic aortic aneurysms ("TAAs") and aortic uni-iliac ("AUI") aneurysms. A TAA may occur downstream the aortic arch, i.e., in the descending aorta. Alternatively, a TAA may occur in the aortic arch itself, where the aorta branches to supply the brachiocephalic, left carotid and subclavian arteries, or may occur in the ascending aorta.

SUMMARY OF APPLICATIONS

In some applications of the present invention, a multi-component endovascular stent system comprises first and second generally tubular stent members configured for in situ anastomosis therebetween. The first and second stent members are shaped so as to define respective first and second interface sections. The first and second interface sections are securely coupleable to each other when the first and second stent members are in respective radially-expanded states. The first interface section is shaped so as to define an opening having a structural circumference. The second interface section is shaped so as to define a neck portion longitudinally flanked by proximal and distal portions. The neck portion is generally radially narrower than the proximal and distal portions.

The first and second stent members comprise a plurality of structural elements. The structural circumference of the first stent member is defined by one or more of the structural elements of the first stent member. When the first and second stent members are coupled together in their respective radially-expanded states, the neck portion of the second interface section is at least in part defined by:

first ones of the structural elements of the second stent member, which are positioned at respective first circumferential locations. Each of at least a portion of the first structural elements is configured to apply, to the structural circumference of the first interface section, a distally- and radially-outwardly-directed force, without applying any proximally-directed force; and separate from the first structural elements of the second stent member, second ones of the structural elements, which are positioned at respective second circumferential locations different from the first circumferential locations. Each of at least a portion of the second structural elements is configured to apply, to the structural circumference of the first interface section, a proximally- and radially-outwardly-directed force, without applying any distally-directed force.

The first and second structural elements collectively apply forces that are directed distally and proximally (and radially outward), thereby coupling the neck portion of the second interface section to the structural circumference of the first interface section. Although the distally-directed forces are not applied at the same circumferential locations as the proximally-directed forces, the forces together provide sufficient support to securely couple the first and second interface sections together.

In general, in hourglass-shaped interfaces between first and second stent members, a neck portion of the second interface section that has a more acute angle (i.e., a lower radius of curvature) provides better fixation with the structural circumference of the first interface section, because of the better confinement of the structural circumference in the apex of the hourglass-shaped interface. However, when the stent members are radially compressed for delivery, a more acute neck portion has a greater risk of undergoing plastic deformation (i.e., exceeding the approximately 6%-9% allowable strain, beyond which the alloy undergoes martensitic, i.e., plastic, deformation), rather than elastic deformation. The techniques of the present invention, by using separate first and second structural elements to provide fixation, provide the neck portion in effect with an acute angle around the structural circumference, without necessarily including any individual stent elements that actually have an acute angle. This reduces the risk that the stent elements of the neck portion may undergo plastic deformation, rather than elastic deformation, when radially compressed for delivery.

For some applications, all of the first structural elements are configured to apply respective distally- and radially-outwardly-directed forces, and all of the second structural elements are configured to apply respective proximally- and radially-outwardly-directed forces. Alternatively, only a portion of the first structural elements and/or the second structural elements are configured to apply the forces, while the remainder of the structural elements do not apply any force to the structural circumference of the first interface section (and, typically, do not make contact with the structural circumference).

For some applications, the first structural elements are arranged in first groups of one to ten (e.g., one to five, such as one to three) circumferentially-adjacent first structural elements, and the second structural elements are arranged in second groups of one to ten (e.g., one to five, such as one to three) circumferentially-adjacent second structural elements. The first and the second groups circumferentially alternate around the neck portion of the second interface section. For example, each group may include exactly one structural element, in which case the first and second structural elements circumferentially alternate around the neck portion.

For some applications, the stent system further comprises a first graft member, which is securely fixed to the first stent member, and/or a second graft member, which is securely fixed to the second stent member. Each of the graft members comprises one or more biologically-compatible substantially blood-impervious flexible sheets, which are securely fixed to the stent members, respectively, either outside or within the stent members.

There is therefore provided, in accordance with an application of the present invention, apparatus including a multi-component endovascular stent system, which includes first and second generally tubular stents members, which (a) are configured to assume respective radially-compressed states for transluminal delivery, and respective radially-expanded states for intraluminal fixation, and (b) include structural elements, wherein the second stent member has proximal and distal ends, wherein the first and the second stent members are shaped so as to define first and second interface sections, respectively, which are securely coupleable to each other when the first and the second stent members are in their respective radially-expanded states, wherein the first interface section is shaped so as to define an opening having a structural circumference defined by one or more of the structural elements of the first stent member, wherein the second interface section is shaped so as to define a neck portion longitudinally flanked by proximal and distal portions, which neck portion is generally radially narrower than the proximal and the distal portions, and wherein, when the first and the second stent members are coupled together in their respective radially-expanded states, the neck portion is at least in part defined by:

first ones of the structural elements of the second stent member, which are positioned at respective first circumferential locations, wherein each of at least a portion of the first structural elements is configured to apply, to the structural circumference of the first interface section, a distally- and radially-outwardly-directed force, without applying any proximally-directed force, and separate from the first structural elements, second ones of the structural elements of the second stent member, which are positioned at respective second circumferential locations different from the first circumferential locations, wherein each of at least a portion of the second structural elements is configured to apply, to the structural circumference of the first interface section, a proximally- and radially-outwardly-directed force, without applying any distally-directed force.

For some applications, the first interface section is positioned at a longitudinal location other than at ends of the first stent member, such that the opening is defined by a lateral wall of the first stent member.

For some applications, the first interface section is positioned at a longitudinal end of the first stent member. For some applications, the first interface section extends along a longitudinal portion of the first stent member longitudinally adjacent to the longitudinal end, which longitudinal portion radially narrows toward the longitudinal end.

For some applications, a length of the structural circumference of the first interface section is less than (e.g., at least 30% less than) a perimeter of a narrowest portion of the neck portion of the second interface section, when the first and the second stent members are in their respective radially-expanded states, and not coupled to each other.

For some applications, the first structural elements are arranged in first groups of one to ten circumferentially-adjacent first structural elements, the second structural elements are arranged in second groups of one to ten circumferentially-adjacent second structural elements, and the first and the second groups circumferentially alternate around the neck portion. For some applications, each of the first groups consists of exactly one of the first structural elements, and each of the second groups consists of exactly one of the second structural elements.

For some applications, the stent system further includes a first graft member, which is securely fixed to the first stent member, and a second graft member, which is securely fixed to the second stent member. For some applications, the stent system further includes a graft member, which is securely fixed to a stent member selected from the group consisting of: the first stent member and the second stent member.

For any of the applications described above, each of all of the first structural elements may be configured to apply, to the structural circumference of the first interface section, the distally- and radially-outwardly-directed force, without applying any proximally-directed force, and each of all of the second structural elements may be configured to apply, to the structural circumference of the first interface section, the proximally- and radially-outwardly-directed force, without applying any distally-directed force.

For any of the applications described above, when the first and the second stent members are in their respective radially-expanded states, at least one of the first structural elements may be shaped so as to define first proximal and first distal portions joined at a first apex, which first proximal portion is configured to apply, to the structural circumference, the distally- and radially-outwardly-directed force, and which first distal portion is configured not to apply any force to the structural circumference. For some applications, when the first and the second stent members are in their respective radially-expanded states, at least one of the second structural elements is shaped so as to define second proximal and second distal portions joined at a second apex, which second distal portion is configured to apply, to the structural circumference, the proximally- and radially-outwardly-directed force, and which second proximal portion is configured not to apply any force to the structural circumference.

For any of the applications described above, a first combined total surface area of contact between the first structural elements and the structural circumference may be at least 15% greater than (e.g., at least 30% greater than) a second combined total surface area of contact between the second structural elements and the structural circumference.

For any of the applications described above, a first combined total surface area of contact between the second structural elements and the structural circumference is at least 15% greater than (e.g., at least 30% greater than) a second combined total surface area of contact between the first structural elements and the structural circumference.

For any of the applications described above, the second interface section may be shaped so as to gradually narrow from the proximal portion to the neck portion and from the distal portion to the neck portion.

For any of the applications described above, a first axial force applied between each of the first structural elements, taken separately, and the structural circumference may be greater than (e.g., at least 30% greater than) a second axial force applied between each of the second structural elements, taken separately, and the structural circumference, when the first and the second stent members are coupled together in their respective radially-expanded states.

For any of the applications described above, a second axial force applied between each of the second structural elements, taken separately, and the structural circumference may be greater than (e.g., at least 30% greater than) a first axial force applied between each of the first structural elements, taken separately, and the structural circumference, when the first and the second stent members are coupled together in their respective radially-expanded states.

There is further provided, in accordance with an application of the present invention, a method including:

providing the multi-component endovascular stent system described above; and deploying the first and the second stent members in a blood vessel of a patient such that the first and the second interface sections are coupled to each other.

The present invention will be more fully understood from the following detailed description of embodiments thereof, taken together with the drawings, in which:

BRIEF DESCRIPTION OF THE DRAWINGS

FIGS. 5A-D are schematic illustrations of the second interface section and the structural circumference of the first interface section of the stent system of FIGS. 1A-B and 2A-B, in accordance with an application of the present invention; and FIG. 6 is a schematic illustration of an alternative neck portion, in accordance with an application of the present invention.

DETAILED DESCRIPTION OF APPLICATIONS

Figure 1A:
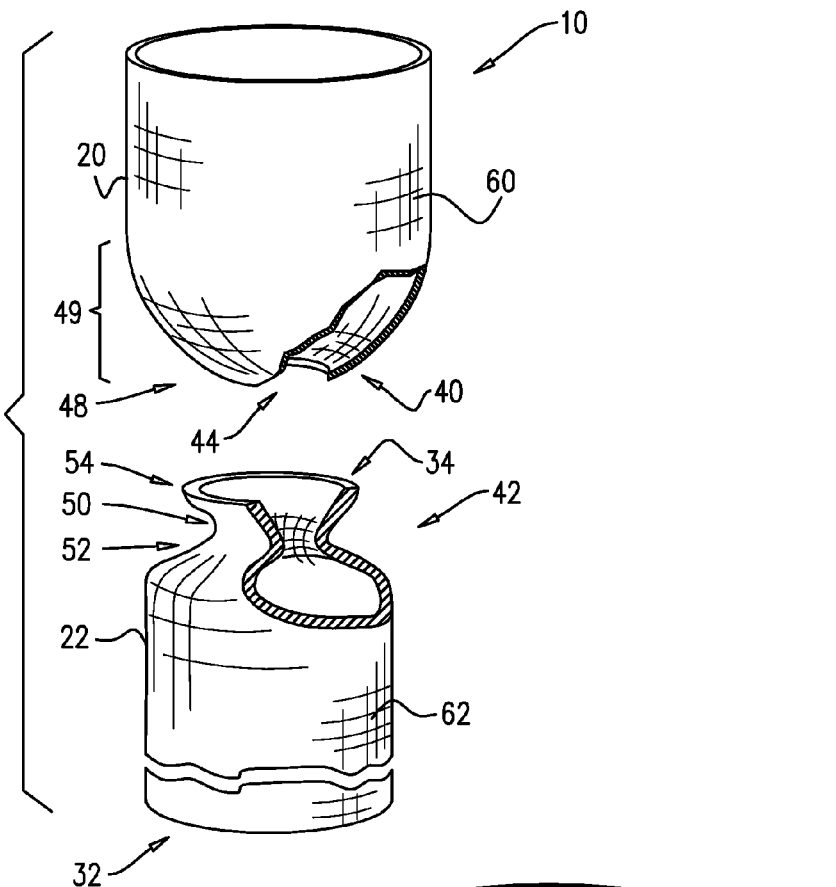
FIGS. 1A-B are schematic illustrations of an end-to-end configuration of a multi-component endovascular stent system, disassembled and assembled, respectively, in accordance with an application of the present invention.
Figure 1B:
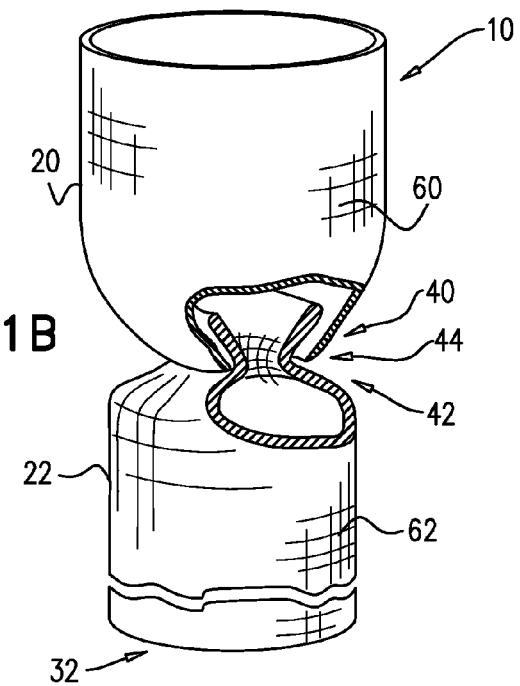

FIGS. 1A-B are schematic illustrations of a multi-component endovascular stent system 10, in accordance with an application of the present invention. FIG. 1A shows the stent system disassembled, and FIG. 1B shows the stent system assembled in an end-to-end arrangement. Stent system 10 comprises first and second generally tubular stent members 20 and 22, which, for some applications, are primary and secondary stent members, respectively. Stent members 20 and 22 are configured to initially be positioned in one or more delivery catheters in respective radially-compressed states for transluminal delivery, and to assume respective radially-expanded states upon being deployed from the delivery catheters for intraluminal fixation. FIGS. 1A-B show the endovascular stent members in their respective radially-expanded states. For some applications, the stent members are heat-set to assume their radially-expanded states.

Stent system 10 is configured for in situ assembly to provide an anastomosis between the first and the second stent members. First and second stent members 20 and 22 are typically sized that they become tightly coupled to each other upon radial expansion of the stent members in situ.

Figure 2A:
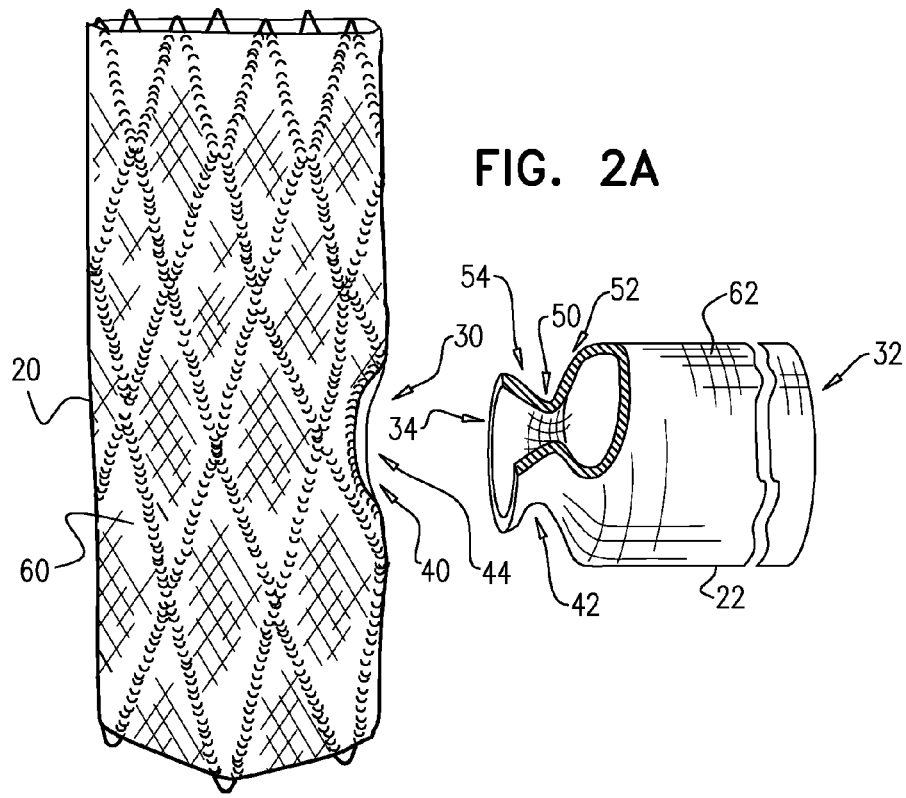
FIGS. 2A-B are schematic illustrations of an end-to-side configuration of the multi-component endovascular stent system of FIGS. 1A-B, in accordance with an application of the present invention.
Figure 2B:
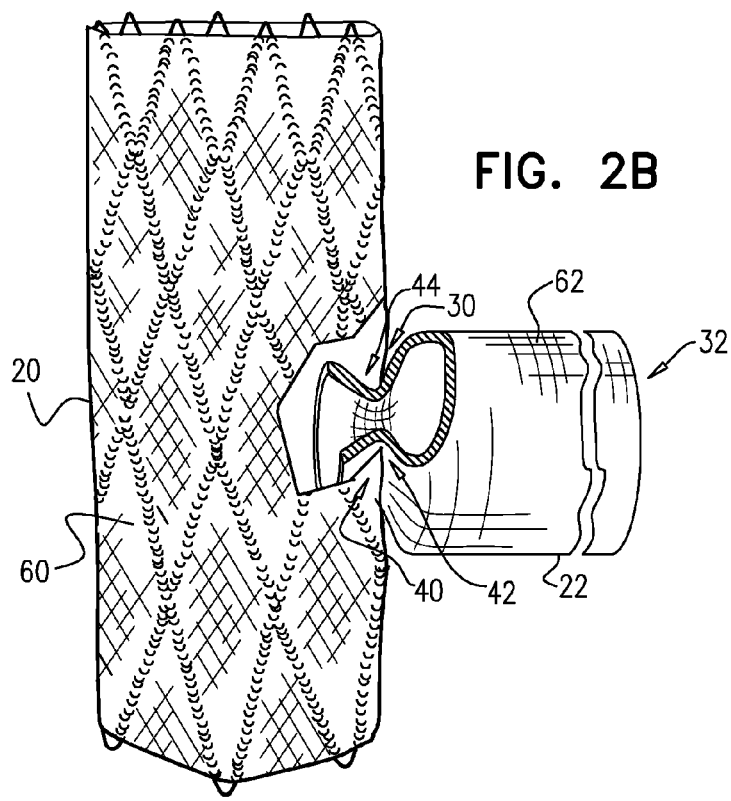
Figure 3A:
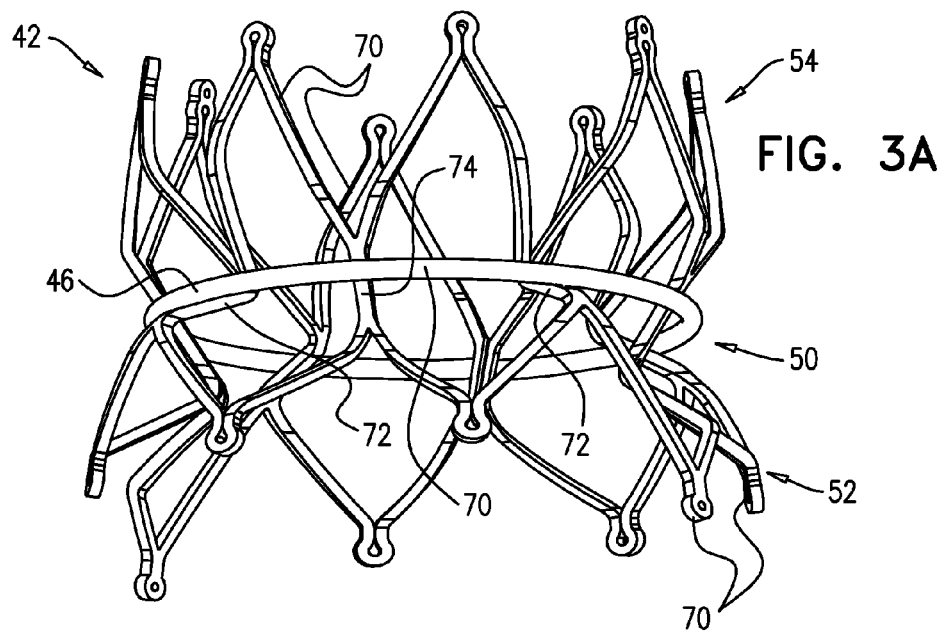
FIGS. 3A-F are schematic illustrations of a second interface section of the stent system of FIGS. 1A-B and 2A-B, in accordance with an application of the present invention.
Figure 3B:
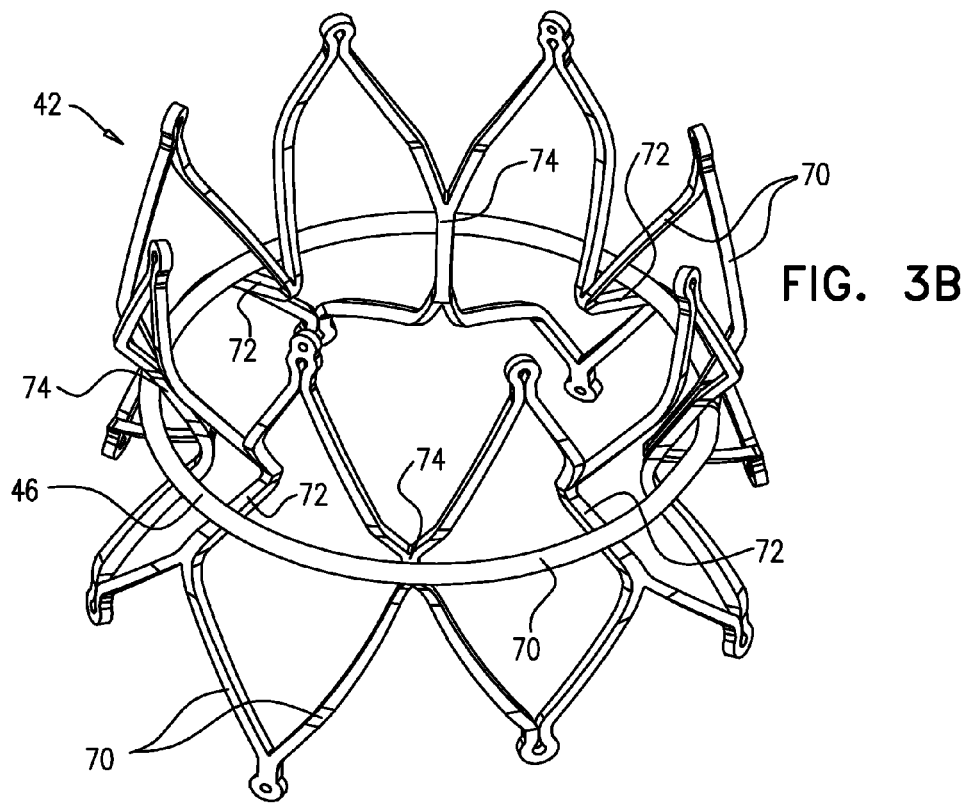
Figure 3C:
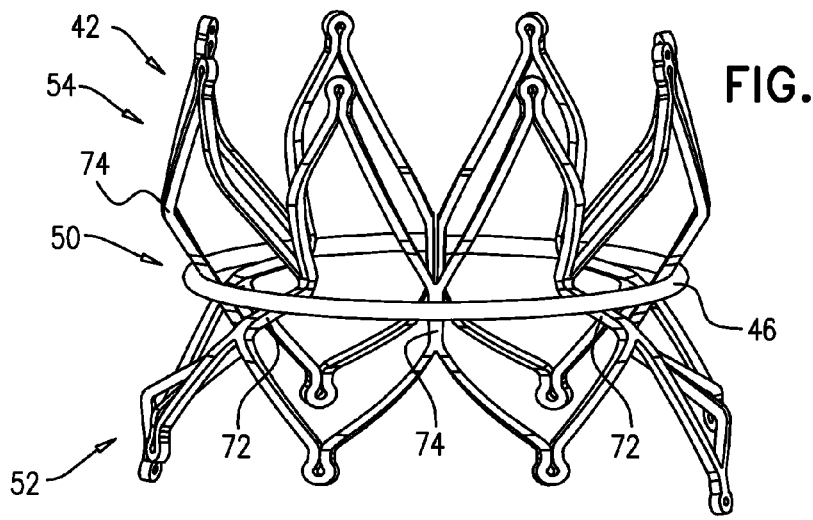
Figure 3D:
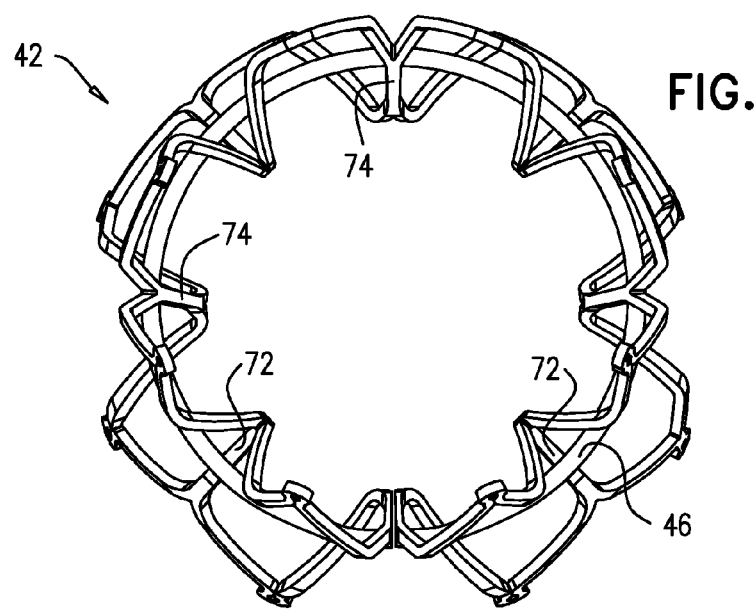
Figure 3E:
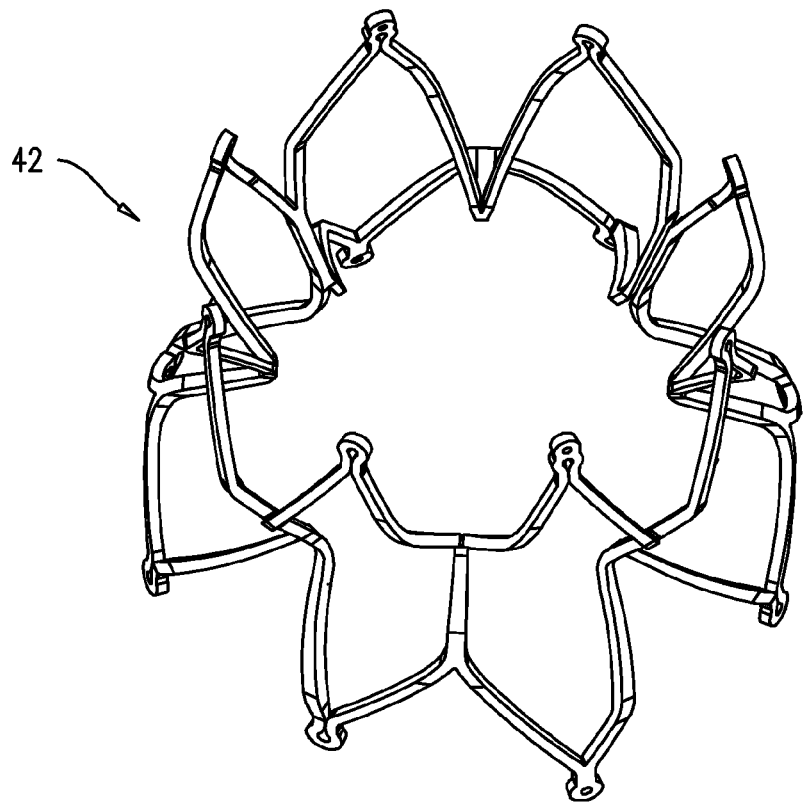
Figure 3F:
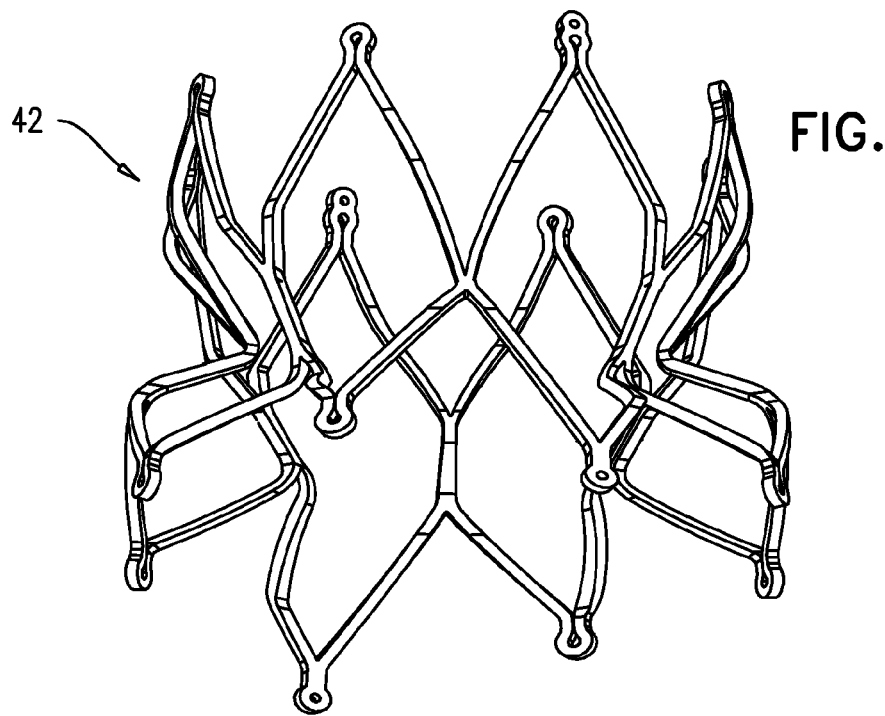

FIGS. 2A-B are schematic illustrations of another configuration of multi-component endovascular stent system 10, in accordance with an application of the present invention. FIG. 2A shows the stent system disassembled, and FIG. 2B shows the stent system assembled in an end-to-side arrangement. In this configuration, a lateral wall of first stent member 20 is shaped so as to define a side-facing fenestration 30, when the stent member is in its radially-expanded state. For some applications, a perimeter of the fenestration is between 10% and 50% of a perimeter of first stent member 20 adjacent the fenestration, when the stent member is in its radially-expanded state. For some applications, stent system 10 implements side-facing fenestration 30, and/or techniques for coupling second stent 22 thereto, in combination with techniques described in PCT Publication WO 2011/007354 and/or in PCT Publication 2011/064782, mutatis mutandis, both of which are incorporated herein by reference.

All of the configurations and techniques described herein may be used with either the end-to-end configuration shown in FIGS. 1A-B or the end-to-side configuration shown in FIG. 2A-B, unless specifically otherwise indicated.

As used in the present application, including in the claims, "tubular" means having the form of an elongated hollow object that defines a conduit therethrough. A "tubular" structure may have varied cross-sections therealong, and the cross-sections are not necessarily circular. For example, one or more of the cross-sections may be generally circular, or generally elliptical but not circular.

Reference is made to both FIGS. 1A-B and 2A-B. First and second stent members 20 and 22 are shaped so as to define first and second interface sections 40 and 42, respectively. First and second interface sections 40 and 42 are securely coupleable to each other when first and second stent members 20 and 22 are in their respective radially-expanded states, thereby immobilizing second stent member 22 with respect to first stent member 20. First and second interface sections 40 and 42 thus may be considered to jointly define an anastomosis section of stent system 10.

First interface section 40 is shaped so as to define an opening 44 having a structural circumference 46 (i.e., a boundary around opening 44). For some applications, the structural circumference is generally circular, as shown in the figures, while for other applications, the structural circumference is elliptical or has another shape.

For some applications, such as shown in FIGS. 2A-B, first interface section 40 is positioned at a longitudinal location other than at ends of first stent member 20, such that opening 44 is defined by a lateral wall of first stent member 20, i.e., corresponds to fenestration 30 mentioned above with reference to FIGS. 2A-B.

For other applications, such as shown in FIGS. 1A-B, first interface section 40 is positioned at a longitudinal end 48 of first stent member 20. For these applications, a plane generally defined by structural circumference 46 may be generally perpendicular to a longitudinal axis of first stent member 20 near longitudinal end 48. For some applications, first interface section 40 extends along a longitudinal portion 49 of first stent member 20 longitudinally adjacent to longitudinal end 48, which longitudinal portion 49 radially narrows toward longitudinal end 48. For some applications, first stent member 20 is bifurcated, and is shaped so as to define one or more longitudinal ends in addition to longitudinal end 48 and a longitudinal end at the opposite end of the stent member (configuration not shown). For example, first stent member 20 may be shaped as shown in FIG. 3 of PCT Publication WO 2010/150208, mutatis mutandis, which publication is incorporated herein by reference.

Second stent member 22 has proximal and distal ends 32 and 34. Second interface section 42 is shaped so as to define a neck portion 50 longitudinally flanked by proximal and distal portions 52 and 54. Neck portion 50 is generally radially narrower than proximal and distal portions 52 and 54. For some applications, such as shown in the figures, second interface section 42 is shaped so as to gradually narrow from proximal portion 52 to neck portion 50 and from distal portion 54 to neck portion 50. Neck portion 50 thus may have an hourglass shape defining two smoothly curved (radially concave) portions. Alternatively, for some applications, second interface section 42 is shaped so as to abruptly narrow from proximal portion 52 to neck portion 50 and from distal portion 54 to neck portion 50. Neck portion 50 thus may have a rectangular (stepped) shape when viewed in cross-section. Further alternatively, for some applications, the transition from one of proximal and distal portions 52 and 54 to neck portion 50 is gradual, while the transition from the other of the proximal and distal portions to the neck portion is abrupt.

For some applications, a length of structural circumference 46 of first interface section 40 is less than (e.g., at least 30% less than) a perimeter of a narrowest portion of neck portion 50 of second interface section 42, when first and second stent members 20 and 22 are in their respective radially-expanded states, and not coupled to each other. In other words, neck 50 is oversized relative to opening 44 of first interface section 40, in order to create good fixation between the first and the second interface sections.

Typically, stent members 20 and 22 are self-expanding. For some applications, stent members 20 and 22 comprise a superelastic metallic alloy, a shape memory metallic alloy, and/or Nitinol. For some applications, first stent member 20 and/or second stent member 22 comprise anchoring elements, for example as described in the above-mentioned '208 publication, mutatis mutandis, e.g., with reference to FIGS. 3, 7A-C, 9A-B, 10A-B, 13, 15A-C, 16, 17, 18, 19, 20A-B, and/or 21A-B thereof.

For some applications, stent system 10 further comprises a first graft member 60, which is securely fixed to first stent member 20. Alternatively or additionally, for some applications, stent system 10 further comprises a second graft member 62, which is securely fixed to second stent member 22. Each of graft members 60 and 62 comprises one or more biologically-compatible substantially blood-impervious flexible sheets, which are securely fixed to stent members 20 and 22, respectively, either outside or within the stent members, such as by stitching, and covers either an external or an internal surface of a portion of the stent members. The flexible sheet may comprise, for example, a polymeric film material (e.g., polytetrafluoroethylene), a polymeric textile material (e.g., woven polyethylene terephthalate (PET)), natural tissue graft (e.g., saphenous vein or collagen), or a combination thereof.

Reference is now made to FIGS. 3A-F, which are schematic illustrations of second interface section 42, in accordance with an application of the present invention. FIGS. 3A-D additionally show structural circumference 46 of first interface section 40, while FIGS. 3E-F do not show the structural circumference. First and second stent members 20 and 22 comprise a plurality of structural elements 70. For some applications, the structural elements are arranged as a plurality of circumferential bands. For some applications, at least some of, e.g., all of, the structural stent elements are interconnected, while for other applications, at least a portion of, e.g., all, of the structural stent elements are not interconnected. For example, circumferential bands may be not directly connected to one another, but instead indirectly connected by the graft members, if provided.

Structural circumference 46 of first stent member 20 is defined by one or more of structural elements 70 of first stent member 20. By way of example, structural circumference 46 is shown in FIGS. 3A-D (and FIGS. 5A-D) as being defined by a single one of structural elements 70, which, for clarity of illustration, are shown highly schematically). Typically, the one or more structural elements of structural circumference 46 are coupled to other structural elements of first stent member 20; for clarity of illustration, these other structural elements are not shown in FIGS. 3A-D (or FIGS. 5A-D).

For some applications, when first and second stent members 20 and 22 are coupled together in their respective radially-expanded states, neck portion 50 of second interface section 42 is at least in part defined by:

first ones 72 of structural elements 70 of second stent member 22, which are positioned at respective first circumferential locations. Each of at least a portion of first structural elements 72 is configured to apply, to structural circumference 46 of first interface section 40, a distally- and radially-outwardly-directed force, without applying any proximally-directed force; and separate from first structural elements 72, second ones 74 of structural elements 70 of second stent member 22, which are positioned at respective second circumferential locations different from the first circumferential locations. Each of at least a portion of second structural elements 74 is configured to apply, to structural circumference 46 of first interface section 40, a proximally- and radially-outwardly-directed force, without applying any distally-directed force.

Together, first and second structural elements 72 and 74 collectively apply forces that are directed distally and proximally (and radially outward), thereby coupling neck portion 50 of second interface section 42 to structural circumference 46 of first interface section 40. Although the distally-directed forces are not applied at the same circumferential locations as the proximally-directed forces, the forces together provide sufficient support to strongly couple the first and second interface sections together.

Typically, during an implantation procedure, first stent member 20 is at least partially radially expanded (at least the portion thereof including first interface section 40). Subsequently, second interface section 42, while still at least partially radially compressed, is placed through structural circumference 46 of first interface section 40. Once properly positioned, second interface section 42 is radially expanded, in order to form a tight coupling with the first interface section. For some applications, the implantation procedure is performed, mutatis mutandis, using techniques described in the above-mentioned '354 publication, with reference to FIGS. 6A-F thereof; and/or the above-mentioned '782 publication, with reference to FIGS. 3A-L, 6A-H, 9A-H, and/or 11A-E thereof.

For some applications, all of first structural elements 72 are configured to apply respective distally- and radially-outwardly-directed forces, and all of second structural elements 74 are configured to apply respective proximally- and radially-outwardly-directed forces, as shown in FIGS. 3A-F (and FIGS. 5A-D). Alternatively, only a portion of first structural elements 72 and/or second structural elements 74 are configured to apply the forces, while the remainder of the structural elements do not apply any force to structural circumference 46 of first interface section 40 (and, typically, do not make contact with structural circumference 46).

Figure 4:
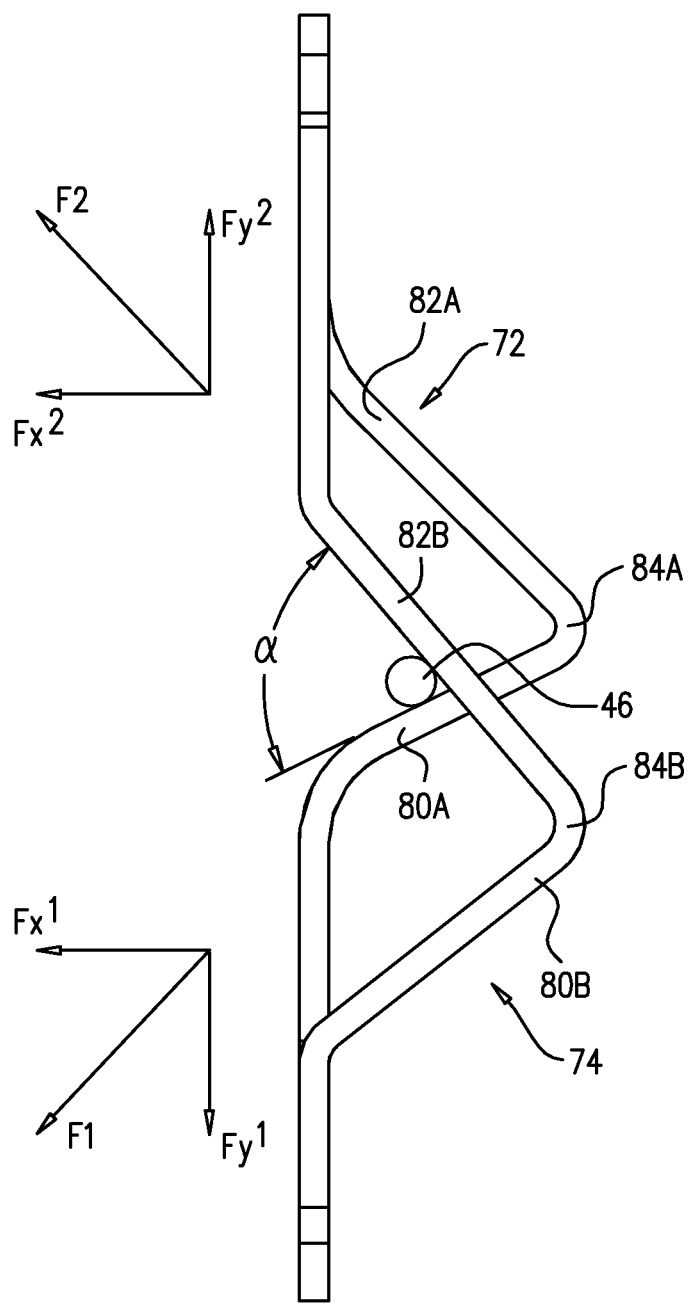
FIG. 4 is a schematic side-view of the second interface section and a structural circumference of a first interface section of the stent system of FIGS. 1A-B and 2A-B, in accordance with an application of the present invention.
Figure 5A:
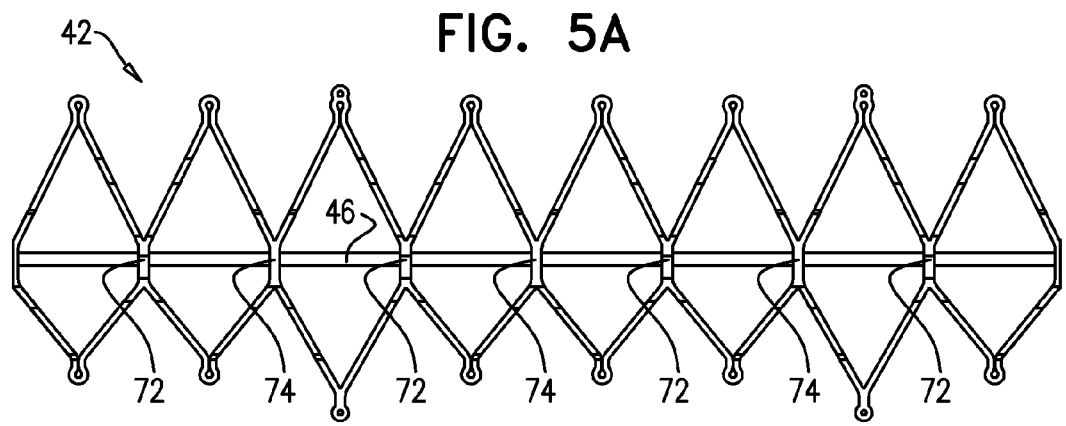
Figure 5B:
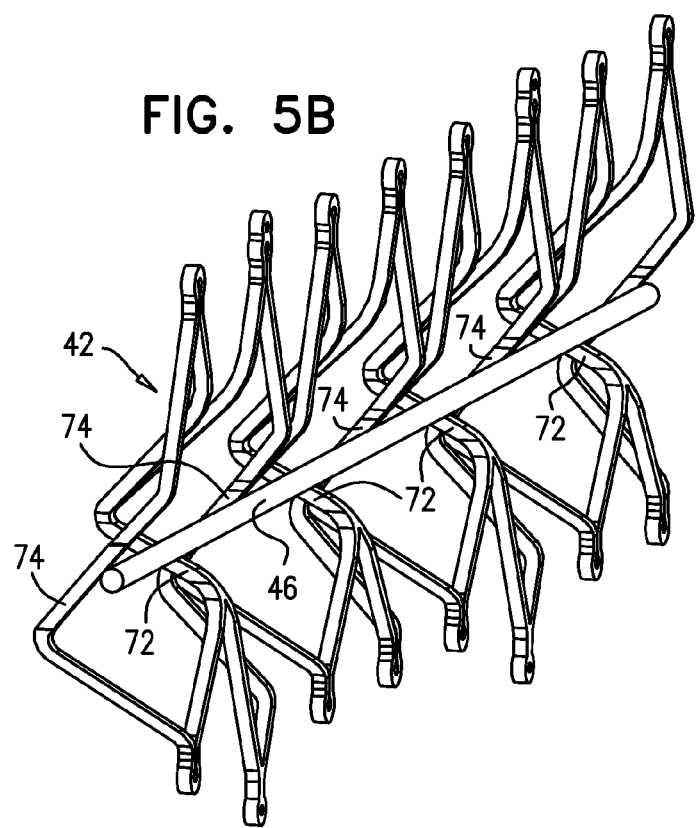

Reference is made to FIG. 4, which is a schematic illustration of second interface section 42 and structural circumference 46 of first interface section 40, in accordance with an application of the present invention. This view shows exactly one of first structural elements 72 and exactly one of second structural elements 74 (the direction of the view is labeled in FIG. 5C). It is noted that first and second structural elements 72 and 74 are not in the same plane, but rather are in respective planes that are generally aligned with respective radii that emanate from a longitudinal axis of the interface section. First structural element 72 applies to structural circumference 46 a first force F1, which is directed distally and radially outwardly, without applying any proximally-directed force. Second structural element 74 applies to structural circumference 46 a second force F2, which is directed proximally and radially outwardly, without applying any distally-directed force.

For some applications, when first and second stent members 20 and 22 are in their respective radially-expanded states:
- at least one of first structural elements 72 is shaped so as to define first proximal and first distal portions 80A and 82A joined at a first apex 84A. First proximal portion 80A is configured to apply, to structural circumference 46, the distally- and radially-outwardly-directed force. First distal portion 82A is configured not to apply any force to structural circumference 46; and/or
- at least one of second structural elements 74 is shaped so as to define second proximal and second distal portions 80B and 82B joined at a second apex 84B. Second distal portion 80B is configured to apply, to structural circumference 46, the proximally- and radially-outwardly-directed force. Second proximal portion 82B is configured not to apply any force to structural circumference 46.

For some applications, first and second structural elements 72 and 74, if projected onto a common plane perpendicular to an axis of structural circumference 46, would define an angle α (alpha) between the elements, facing the structural circumference, having a value of less than 120 degrees, such as less than 60 degrees.

Reference is now made to FIGS. 5A-D, which are schematic illustrations of second interface section 42 and structural circumference 46 of first interface section 40, in accordance with an application of the present invention. In these figures, for clarity of illustration, first and second interface sections 40 and 42 have been cut open along a line parallel to the longitudinal axis of interface sections and laid straight.

Reference is made to FIGS. 3A-F and 5A-D. For some applications, first structural elements 72 are arranged in first groups of one to ten (e.g., one to five, such as one to three) circumferentially-adjacent first structural elements 72, and second structural elements 74 are arranged in second groups of one to ten (e.g., one to five, such as one to three) circumferentially-adjacent second structural elements 74. The first and the second groups circumferentially alternate around neck portion 50 of second interface section 42. For example, each group may include exactly one structural element, in which case first and second structural elements 72 and 74 circumferentially alternate around the neck portion, as shown in FIGS. 3A-F and 5A-D.

For some applications, a first combined total surface area of contact between first structural elements 72 and structural circumference 46 is greater than (e.g., at least 15% greater than, such as at least 30% greater than) a second combined total surface area of contact between second structural elements 74 and structural circumference 46. For some applications, this greater surface area is achieved by:
- configuring first structural elements 72 to be wider (in a circumferential direction) than second structural elements 74; and/or
- configuring second interface section 42 such that more first structural elements 72 come in contact with structural circumference 46 than do second structural elements 74.

This configuration may be useful in applications in which it is more necessary to prevent movement of second interface section 42 in a distal direction than in a proximal direction, e.g., because blood flows in the distal direction upon implantation of stent system 10.

For some applications, a first combined total surface area of contact between second structural elements 74 and structural circumference 46 is greater than (e.g., at least 15% greater than, such as at least 30% greater than) a second combined total surface area of contact between first structural elements 72 and structural circumference 46. For some applications, this greater surface area is achieved by:
- configuring second structural elements 74 to be wider (in a circumferential direction) than first structural elements 72; and/or
- configuring second interface section 42 such that more second structural elements 74 come in contact with structural circumference 46 than do first structural elements 72.

This configuration may be useful in applications in which it is more necessary to prevent movement of second interface section 42 in a proximal direction than in a distal direction, e.g., because blood flows in the proximal direction upon implantation of stent system 10.

For some applications, a first axial force applied between each of first structural elements 72, taken separately (i.e., on a per-element basis), and structural circumference 46 is greater than (e.g., at least 15% greater than, or at least 30% greater than) a second axial force applied between each of second structural elements 74, taken separately, and structural circumference 46, when first and second stent members 20 and 22 are coupled together in their respective radially-expanded states. Optionally, for these application, neck portion 50 is shaped so as to define a different number of (e.g., fewer) first structural elements 72 than second structural elements 74.

For some applications, a first maximum axial force that can applied between each of first structural elements 72, taken separately (i.e., on a per-element basis), and structural circumference 46, without any elements 72 undergoing plastic deformation, is greater than (e.g., at least 15% greater than, or at least 30% greater than) a second maximum axial force that can be applied between each of second structural elements 74, taken separately, and structural circumference 46, without any elements 74 undergoing plastic deformation, when first and second stent members 20 and 22 are coupled together in their respective radially-expanded states. Optionally, for these application, neck portion 50 is shaped so as to define a different number of (e.g., fewer) first structural elements 72 than second structural elements 74.

For some applications, a second axial force applied between each of second structural elements 74, taken separately (i.e., on a per-element basis), and structural circumference 46 is greater than (e.g., at least 15% greater than, or at least 30% greater than) a first axial force applied between each of first structural elements 72, taken separately, and structural circumference 46, when first and second stent members 20 and 22 are coupled together in their respective radially-expanded states. Optionally, for these application, neck portion 50 is shaped so as to define a different number of (e.g., more) first structural elements 72 than second structural elements 74.

For some applications, a second maximum axial force that can applied between each of second structural elements 74, taken separately (i.e., on a per-element basis), and structural circumference 46, without any elements 74 undergoing plastic deformation, is greater than (e.g., at least 15% greater than, or at least 30% greater than) a first maximum axial force that can be applied between each of first structural elements 72, taken separately, and structural circumference 46, without any elements 72 undergoing plastic deformation, when first and second stent members 20 and 22 are coupled together in their respective radially-expanded states. Optionally, for these application, neck portion 50 is shaped so as to define a different number of (e.g., more) first structural elements 72 than second structural elements 74.

Reference is now made to FIG. 6, which is a schematic illustration of an alternative neck portion 146, in accordance with an application of the present invention. In this configuration of neck portion 146, unlike in the other configurations described herein, individual ones of structural elements 70 apply, to structural circumference 46, both (a) a distally- and radially-outwardly-directed force and (b) a proximally- and radially-outwardly-directed force. In order to apply these forces, each of structural elements 70 is shaped so as to define proximal and distal portions 180 and 182 joined at an apex 184. So as to provide good fixation of neck portion 146 to structural circumference 46, proximal and distal portions 180 and 182 typically define an angle β (beta) therebetween of less than 150 degrees, and apex 184 typically has a radius of curvature of less than 50% of the radius of the neck portion. Although this configuration generally provides good fixation, the acuteness of angle β (beta) and low radius of curvature of apex 184 generally increase the risk of plastic deformation, compared to the other configurations of the neck portion described herein.

Stent system 10 may be deployed alone, or as a component of a larger stent system comprising additional stents, for example as described with reference to FIGS. 4E and/or 21B of the '208 publication, mutatis mutandis, or in PCT Publication WO 08/107885, mutatis mutandis, which is incorporated herein by reference. For some applications, stent system 10 defines a single lumen, while for other applications, the stent system 10 defines a plurality of lumen, e.g., is bifurcated, such as described with reference to FIG. 3 of the above-mentioned '208 publication, mutatis mutandis.

For some applications, endovascular stent system 10 may be deployed via an iliac artery and the aorto-iliac bifurcation, or via a subclavian artery. For some applications, endovascular stent system 10 is deployed in the aorta, or in another blood vessel, such as another artery, e.g., an aneurysmatic artery, such as an aneurysmatic iliac artery.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

PCT Application PCT/IL2008/000287, filed Mar. 5, 2008, which published as PCT Publication WO 2008/107885 to Shalev et al., and U.S. application Ser. No. 12/529,936 in the national stage thereof, which published as US Patent Application Publication 2010/0063575 to Shalev et al.

U.S. Provisional Application 60/892,885, filed Mar. 5, 2007

U.S. Provisional Application 60/991,726, filed Dec. 2, 2007

U.S. Provisional Application 61/219,758, filed Jun. 23, 2009

U.S. Provisional Application 61/221,074, filed Jun. 28, 2009

PCT Application PCT/IB2010/052861, filed Jun. 23, 2010, which published as PCT Publication WO 2010/150208

PCT Application PCT/IL2010/000564, filed Jul. 14, 2010, which published as PCT Publication WO 2011/007354

PCT Application PCT/IL2010/000917, filed Nov. 4, 2010, which published as PCT Publication WO 2011/055364

PCT Application PCT/IL2010/000999, filed Nov. 30, 2010, which published as PCT Publication WO 2011/064782

PCT Application PCT/IL2010/001018, filed Dec. 2, 2010, which published as PCT Publication WO 2011/067764

PCT Application PCT/IL2010/001037, filed Dec. 8, 2010, which published as PCT Publication WO 2011/070576

PCT Application PCT/IL2011/000135, filed Feb. 8, 2011, which published as PCT Publication WO 2011/095979

U.S. application Ser. No. 13/031,871, filed Feb. 22, 2011, which published as US Patent Application Publication 2011/0208289

U.S. Provisional Application 61/496,613, filed Jun. 14, 2011

U.S. Provisional Application 61/499,195, filed Jun. 21, 2011

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising a multi-component endovascular stent system, which comprises first and second generally tubular stents members, which (a) are configured to assume respective radially-compressed states for transluminal delivery, and respective radially-expanded states for intraluminal fixation, and (b) comprise structural elements, wherein the second stent member has proximal and distal ends, wherein the first and the second stent members are shaped so as to define first and second interface sections, respectively, which are securely coupleable to each other when the first and the second stent members are in their respective radially-expanded states, wherein the first interface section is shaped so as to define an opening having a structural circumference defined by one or more of the structural elements of the first stent member, wherein the second interface section is shaped so as to define a neck portion longitudinally flanked by proximal and distal portions, which neck portion is generally radially narrower than the proximal and the distal portions, wherein, when the first and the second stent members are coupled together in their respective radially-expanded states, the neck portion is at least in part defined by:

first ones of the structural elements of the second stent member, which are positioned at respective first circumferential locations, wherein each of at least a portion of the first structural elements longitudinally spans the structural circumference, and is configured to apply, to the structural circumference of the first interface section, a distally- and radially-outwardly-directed force, without applying any proximally-directed force, and separate from the first structural elements, second ones of the structural elements of the second stent member, which are positioned at respective second circumferential locations different from the first circumferential locations, wherein each of at least a portion of the second structural elements longitudinally spans the structural circumference, and is configured to apply, to the structural circumference of the first interface section, a proximally- and radially-outwardly-directed force, without applying any distally-directed force, and wherein all of the first circumferential locations are circumferentially offset from all of the second circumferential locations.

2. The apparatus according to claim 1, wherein the first interface section is positioned at a longitudinal location other than at ends of the first stent member, such that the opening is defined by a lateral wall of the first stent member.

3. The apparatus according to claim 1, wherein the first interface section is positioned at a longitudinal end of the first stent member.

4. The apparatus according to claim 3, wherein the first interface section extends along a longitudinal portion of the first stent member longitudinally adjacent to the longitudinal end, which longitudinal portion radially narrows toward the longitudinal end.

5. The apparatus according to claim 1, wherein a length of the structural circumference of the first interface section is less than a perimeter of a narrowest portion of the neck portion of the second interface section, when the first and the second stent members are in their respective radially-expanded states, and not coupled to each other.

6. The apparatus according to claim 5, wherein the length of the structural circumference is at least 30% less than the perimeter of the narrowest portion of the neck portion.

7. Apparatus comprising a multi-component endovascular stent system, which comprises first and second generally tubular stents members, which (a) are configured to assume respective radially-compressed states for transluminal delivery, and respective radially-expanded states for intraluminal fixation, and (b) comprise structural elements, wherein the second stent member has proximal and distal ends, wherein the first and the second stent members are shaped so as to define first and second interface sections, respectively, which are securely coupleable to each other when the first and the second stent members are in their respective radially-expanded states, wherein the first interface section is shaped so as to define an opening having a structural circumference defined by one or more of the structural elements of the first stent member, wherein the second interface section is shaped so as to define a neck portion longitudinally flanked by proximal and distal portions, which neck portion is generally radially narrower than the proximal and the distal portions, wherein, when the first and the second stent members are coupled together in their respective radially-expanded states, the neck portion is at least in part defined by:

first ones of the structural elements of the second stent member, which are positioned at respective first circumferential locations, wherein each of at least a portion of the first structural elements is configured to apply, to the structural circumference of the first interface section, a distally- and radially-outwardly-directed force, without applying any proximally-directed force, and separate from the first structural elements, second ones of the structural elements of the second stent member, which are positioned at respective second circumferential locations different from the first circumferential locations, wherein each of at least a portion of the second structural elements is configured to apply, to the structural circumference of the first interface section, a proximally- and radially-outwardly-directed force, without applying any distally-directed force, wherein all of the first circumferential location are circumferentially offset from all of the second circumferential locations, and wherein the first structural elements are arranged in first groups of one to ten circumferentially-adjacent first structural elements, wherein the second structural elements are arranged in second groups of one to ten circumferentially-adjacent second structural elements, and wherein the first and the second groups circumferentially alternate around the neck portion.

8. The apparatus according to claim 7, wherein each of the first groups consists of exactly one of the first structural elements, and wherein each of the second groups consists of exactly one of the second structural elements.

9. The apparatus according to claim 1, wherein the stent system further comprises a first graft member, which is securely fixed to the first stent member, and a second graft member, which is securely fixed to the second stent member.

10. The apparatus according to claim 1, wherein the stent system further comprises a graft member, which is securely fixed to a stent member selected from the group consisting of: the first stent member and the second stent member.

11. The apparatus according to claim 1, wherein each of all of the first structural elements is configured to apply, to the structural circumference of the first interface section, the distally- and radially-outwardly-directed force, without applying any proximally-directed force, and wherein each of all of the second structural elements is configured to apply, to the structural circumference of the first interface section, the proximally- and radially-outwardly-directed force, without applying any distally-directed force.

12. The apparatus according to claim 1, wherein, when the first and the second stent members are in their respective radially-expanded states, at least one of the first structural elements is shaped so as to define first proximal and first distal portions joined at a first apex, which first proximal portion is configured to apply, to the structural circumference, the distally- and radially-outwardly-directed force, and which first distal portion is configured not to apply any force to the structural circumference.

13. Apparatus comprising a multi-component endovascular stent system, which comprises first and second generally tubular stents members, which (a) are configured to assume respective radially-compressed states for transluminal delivery, and respective radially-expanded states for intraluminal fixation, and (b) comprise structural elements, wherein the second stent member has proximal and distal ends, wherein the first and the second stent members are shaped so as to define first and second interface sections, respectively, which are securely coupleable to each other when the first and the second stent members are in their respective radially-expanded states, wherein the first interface section is shaped so as to define an opening having a structural circumference defined by one or more of the structural elements of the first stent member, wherein the second interface section is shaped so as to define a neck portion longitudinally flanked by proximal and distal portions, which neck portion is generally radially narrower than the proximal and the distal portions, wherein, when the first and the second stent members are coupled together in their respective radially-expanded states, the neck portion is at least in part defined by:

first ones of the structural elements of the second stent member, which are positioned at respective first circumferential locations, wherein each of at least a portion of the first structural elements is configured to apply, to the structural circumference of the first interface section, a distally- and radially-outwardly-directed force, without applying any proximally-directed force, and separate from the first structural elements, second ones of the structural elements of the second stent member, which are positioned at respective second circumferential locations different from the first circumferential locations, wherein each of at least a portion of the second structural elements is configured to apply, to the structural circumference of the first interface section, a proximally- and radially-outwardly-directed force, without applying any distally-directed force, wherein all of the first circumferential locations are circumferentially offset from all of the second circumferential locations, wherein, when the first and the second stent members are in their respective radially-expanded states, at least one of the first structural elements is shaped so as to define first proximal and first distal portions joined at a first apex, which first proximal portion is configured to apply, to the structural circumference, the distally- and radially-outwardly-directed force, and which first distal portion is configured not to apply any force to the structural circumference, and wherein, when the first and the second stent members are in their respective radially-expanded states, at least one of the second structural elements is shaped so as to define second proximal and second distal portions joined at a second apex, which second distal portion is configured to apply, to the structural circumference, the proximally- and radially-outwardly-directed force, and which second proximal portion is configured not to apply any force to the structural circumference.

14. The apparatus according to claim 1, wherein a first combined total surface area of contact between the first structural elements and the structural circumference is at least 15% greater than a second combined total surface area of contact between the second structural elements and the structural circumference.

15. The apparatus according to claim 14, wherein the first combined total surface area of contact is at least 30% greater than the second combined total surface area of contact.

16. The apparatus according to claim 1, wherein a first combined total surface area of contact between the second structural elements and the structural circumference is at least 15% greater than a second combined total surface area of contact between the first structural elements and the structural circumference.

17. The apparatus according to claim 16, wherein the first combined total surface area of contact is at least 30% greater than the second combined total surface area of contact.

18. The apparatus according to claim 1, wherein the second interface section is shaped so as to gradually narrow from the proximal portion to the neck portion and from the distal portion to the neck portion.

19. The apparatus according to claim 1, wherein a first axial force applied between each of the first structural elements, taken separately, and the structural circumference is greater than a second axial force applied between each of the second structural elements, taken separately, and the structural circumference, when the first and the second stent members are coupled together in their respective radially-expanded states.

20. The apparatus according to claim 19, wherein the first axial force is at least 30% greater than the second axial force.

21. The apparatus according to claim 1, wherein a second axial force applied between each of the second structural elements, taken separately, and the structural circumference is greater than a first axial force applied between each of the first structural elements, taken separately, and the structural circumference, when the first and the second stent members are coupled together in their respective radially-expanded states.

22. The apparatus according to claim 21, wherein the second axial force is at least 30% greater than the first axial force.

23. A method comprising:

providing a multi-component endovascular stent system, which includes first and second generally tubular stents members, which (a) are configured to assume respective radially-compressed states for transluminal delivery, and respective radially-expanded states for intraluminal fixation, and (b) comprise structural elements, wherein the second stent member has proximal and distal ends, wherein the first and the second stent members are shaped so as to define first and second interface sections, respectively, which are securely coupleable to each other when the first and the second stent members are in their respective radially-expanded states, wherein the first interface section is shaped so as to define an opening having a structural circumference defined by one or more of the structural elements of the first stent member, wherein the second interface section is shaped so as to define a neck portion longitudinally flanked by proximal and distal portions, which neck portion is generally radially narrower than the proximal and the distal portions, and wherein, when the first and the second stent members are coupled together in their respective radially-expanded states, the neck portion is at least in part defined by: (a) first ones of the structural elements of the second stent member, which are positioned at respective first circumferential locations, wherein each of at least a portion of the first structural elements longitudinally spans the structural circumference, and is configured to apply, to the structural circumference of the first interface section, a distally- and radially-outwardly-directed force, without applying any proximally-directed force, and (b) separate from the first structural elements of the second stent member, second ones of the structural elements, which are positioned at respective second circumferential locations different from the first circumferential locations, wherein each of at least a portion of the second structural elements longitudinally spans the structural circumference, and is configured to apply, to the structural circumference of the first interface section, a proximally- and radially-outwardly-directed force, without applying any distally-directed force wherein all of the first circumferential locations are circumferentially offset from all of the second circumferential locations; and deploying the first and the second stent members in a blood vessel of a patient such that the first and the second interface sections are coupled to each other.

24. Apparatus comprising a multi-component endovascular stent system, which comprises first and second generally tubular stents members, which (a) are configured to assume respective radially-compressed states for transluminal delivery, and respective radially-expanded states for intraluminal fixation, and (b) comprise structural elements, wherein the second stent member has proximal and distal ends, wherein the first and the second stent members are shaped so as to define first and second interface sections, respectively, which are securely coupleable to each other when the first and the second stent members are in their respective radially-expanded states, wherein the first interface section is shaped so as to define an opening having a structural circumference defined by one or more of the structural elements of the first stent member, wherein the second interface section is shaped so as to define a neck portion longitudinally flanked by proximal and distal portions, which neck portion is generally radially narrower than the proximal and the distal portions, and wherein, when the first and the second stent members are coupled together in their respective radially-expanded states, the neck portion is at least in part defined by:

first ones of the structural elements of the second stent member, which are positioned at respective first circumferential locations, wherein each of at least a portion of the first structural elements is configured to apply, to the structural circumference of the first interface section, a distally- and radially-outwardly-directed force, without applying any proximally-directed force, and wherein at least one of the first structural elements is shaped so as to define first proximal and first distal portions joined at a first apex, and separate from the first structural elements, second ones of the structural elements of the second stent member, which are positioned at respective second circumferential locations different from the first circumferential locations, wherein each of at least a portion of the second structural elements is configured to apply, to the structural circumference of the first interface section, a proximally- and radially-outwardly-directed force, without applying any distally-directed force, wherein at least one of the second structural elements is shaped so as to define second proximal and second distal portions joined at a second apex, and wherein the first and the second apexes are disposed at longitudinally different positions, and wherein all of the first circumferential locations are circumferentially offset from all of the second circumferential locations.

25. The apparatus according to claim 24, wherein the first and the second apexes are disposed on longitudinally-opposite sides of the structural circumference, when the first and the second stent members are coupled together in their respective radially-expanded states.

26. The apparatus according to claim 1, wherein the first structural elements are arranged in first groups of one to ten circumferentially-adjacent first structural elements, wherein the second structural elements are arranged in second groups of one to ten circumferentially-adjacent second structural elements, and wherein the first and the second groups circumferentially alternate around the neck portion.

27. The apparatus according to claim 12, wherein, when the first and the second stent members are in their respective radially-expanded states, at least one of the second structural elements is shaped so as to define second proximal and second distal portions joined at a second apex, which second distal portion is configured to apply, to the structural circumference, the proximally- and radially-outwardly-directed force, and which second proximal portion is configured not to apply any force to the structural circumference.

* * * * *